(12) United States Patent
Alfrhan

(10) Patent No.: US 9,345,604 B2
(45) Date of Patent: May 24, 2016

(54) PERCUTANEOUS INTRAGASTRIC BALLOON DEVICE AND METHOD

(76) Inventor: Almuhannad Alfrhan, Randolph, NE (US)

( * ) Notice: Subject to any disclaimer, the term of this patent is extended or adjusted under 35 U.S.C. 154(b) by 1825 days.

(21) Appl. No.: 11/162,889

(22) Filed: Sep. 27, 2005

(65) Prior Publication Data

US 2006/0271088 A1  Nov. 30, 2006

Related U.S. Application Data

(60) Provisional application No. 60/676,641, filed on May 2, 2005.

(51) Int. Cl.
*A61F 5/00* (2006.01)

(52) U.S. Cl.
CPC .............. *A61F 5/003* (2013.01); *A61F 5/0043* (2013.01)

(58) Field of Classification Search
CPC ................. A61B 2017/00818; A61F 5/0003; A61F 5/0043
USPC .................................................. 606/191, 192
See application file for complete search history.

(56) References Cited

U.S. PATENT DOCUMENTS

| | | | |
|---|---|---|---|
| 2,687,131 A | 8/1954 | Raiche | |
| 3,831,583 A * | 8/1974 | Edmunds et al. | 128/899 |
| 4,057,065 A | 11/1977 | Thow | |
| 4,133,315 A | 1/1979 | Berman et al. | |
| 4,246,893 A | 1/1981 | Berson | |
| 4,315,513 A | 2/1982 | Nawash et al. | |
| 4,416,267 A | 11/1983 | Garren et al. | |
| 4,485,805 A | 12/1984 | Foster, Jr. | |
| 4,592,339 A | 6/1986 | Kuzmak et al. | |
| 4,624,657 A | 11/1986 | Gould et al. | |
| 4,666,433 A | 5/1987 | Parks | |
| 4,694,827 A | 9/1987 | Weiner | |
| 4,723,547 A | 2/1988 | Kullas et al. | |
| 4,739,758 A | 4/1988 | Lai et al. | |
| 4,861,334 A | 8/1989 | Nawaz | |
| 4,899,747 A | 2/1990 | Garren et al. | |
| 4,911,163 A * | 3/1990 | Fina | 606/127 |
| 4,990,139 A * | 2/1991 | Jang | 604/101.01 |
| 5,074,846 A * | 12/1991 | Clegg et al. | 604/164.1 |
| 5,084,061 A | 1/1992 | Gau et al. | |
| 5,226,429 A | 7/1993 | Kuzmak | |

(Continued)

FOREIGN PATENT DOCUMENTS

| | | |
|---|---|---|
| EP | 1366716 | 12/2003 |
| EP | 1671590 | 6/2006 |

(Continued)

*Primary Examiner* — Elizabeth Houston
*Assistant Examiner* — Michael Mendoza
(74) *Attorney, Agent, or Firm* — Barbara A. Wrigley; Fox Rothschild LLP

(57) ABSTRACT

Intragastric balloon devices and methods for performing percutaneous gastronomy in the stomach of a patient are disclosed. The intragastric balloon device can include a support catheter, a main balloon member for use in reducing the functional gastric capacity of the patient's stomach, a support balloon member for anchoring the intragastric balloon device to the gastric wall of the patient, and an inflation mechanism for use in selectively inflating the main and support balloon members. In certain embodiments, an optional insertion device can be provided to facilitate percutaneous insertion and implantation of the intragastric balloon device within the patient.

2 Claims, 24 Drawing Sheets

(56) References Cited

U.S. PATENT DOCUMENTS

| | | | |
|---|---|---|---|
| 5,234,454 A | 8/1993 | Bangs | |
| 5,259,399 A | 11/1993 | Brown | |
| 5,401,241 A * | 3/1995 | Delany | 604/43 |
| 5,601,604 A | 2/1997 | Vincent | |
| 5,656,013 A * | 8/1997 | Yoon | 600/207 |
| 5,697,946 A * | 12/1997 | Hopper et al. | 606/185 |
| 5,860,952 A | 1/1999 | Quinn | |
| RE36,176 E | 3/1999 | Kuzmak | |
| 5,993,473 A | 11/1999 | Chan et al. | |
| 6,102,992 A | 8/2000 | Berg et al. | |
| 6,454,785 B2 | 9/2002 | De Hoyos Garza | |
| 6,579,301 B1 | 6/2003 | Bales et al. | |
| 6,627,206 B2 | 9/2003 | Lloyd | |
| 6,733,512 B2 | 5/2004 | McGhan | |
| 6,981,980 B2 | 1/2006 | Sampson et al. | |
| 7,056,305 B2 | 6/2006 | Garza Alvarez | |
| 7,066,945 B2 | 6/2006 | Hashiba et al. | |
| 7,156,860 B2 * | 1/2007 | Wallsten | 606/192 |
| 7,214,233 B2 | 5/2007 | Gannoe et al. | |
| 2001/0037127 A1 | 11/2001 | DeHoyos Garza | |
| 2002/0055757 A1 | 5/2002 | Torre et al. | |
| 2002/0169464 A1 | 11/2002 | Latour | |
| 2003/0078611 A1 | 4/2003 | Hashiba et al. | |
| 2003/0158564 A1 | 8/2003 | Benchetrit | |
| 2003/0158569 A1 | 8/2003 | Wazne | |
| 2003/0208212 A1 | 11/2003 | Cigaina | |
| 2004/0024363 A1 | 2/2004 | Goldberg | |
| 2004/0030347 A1 | 2/2004 | Gannoe | |
| 2004/0044353 A1 | 3/2004 | Gannoe | |
| 2004/0044354 A1 | 3/2004 | Gannoe et al. | |
| 2004/0044357 A1 | 3/2004 | Gannoe | |
| 2004/0059289 A1 | 3/2004 | Garza Alvarez | |
| 2004/0088008 A1 | 5/2004 | Gannoe | |
| 2004/0147874 A1 | 7/2004 | Kliem | |
| 2004/0148034 A1 | 7/2004 | Kagan et al. | |
| 2004/0153106 A1 | 8/2004 | Dudai | |
| 2004/0186502 A1 | 9/2004 | Sampson et al. | |
| 2004/0186503 A1 | 9/2004 | DeLegge | |
| 2004/0230137 A1 | 11/2004 | Mouton | |
| 2004/0267288 A1 | 12/2004 | Byrum et al. | |
| 2004/0267291 A1 | 12/2004 | Byrum et al. | |
| 2004/0267292 A1 | 12/2004 | Byrum et al. | |
| 2004/0267293 A1 | 12/2004 | Byrum et al. | |
| 2004/0267378 A1 | 12/2004 | Gazi et al. | |
| 2005/0002984 A1 | 1/2005 | Byrum et al. | |
| 2005/0070937 A1 | 3/2005 | Jambor et al. | |
| 2005/0075652 A1 | 4/2005 | Byrum et al. | |
| 2005/0137480 A1 | 6/2005 | Alt et al. | |
| 2005/0143765 A1 | 6/2005 | Bachmann et al. | |
| 2005/0143766 A1 | 6/2005 | Bachmann et al. | |
| 2005/0165432 A1 * | 7/2005 | Heinrich | 606/167 |
| 2005/0183730 A1 | 8/2005 | Byrum | |
| 2005/0187566 A1 | 8/2005 | Byrum | |
| 2005/0216040 A1 | 9/2005 | Gertner | |
| 2005/0267406 A1 | 12/2005 | Hassler, Jr. | |
| 2005/0267500 A1 | 12/2005 | Hassler, Jr. et al. | |
| 2005/0277960 A1 | 12/2005 | Hassler, Jr. et al. | |
| 2005/0277963 A1 | 12/2005 | Fields | |
| 2005/0283172 A1 | 12/2005 | Conlon | |
| 2005/0283180 A1 | 12/2005 | Conlon | |
| 2006/0015125 A1 | 1/2006 | Swain | |
| 2006/0025799 A1 | 2/2006 | Basu | |
| 2006/0259061 A1 | 11/2006 | Kick | |
| 2006/0271088 A1 | 11/2006 | Alfrhan | |
| 2007/0060940 A1 | 3/2007 | Brazzini | |
| 2007/0078476 A1 | 4/2007 | Hull | |
| 2007/0083224 A1 | 4/2007 | Hively | |
| 2007/0100367 A1 | 5/2007 | Quijano | |
| 2007/0123809 A1 | 5/2007 | Weiss | |
| 2008/0097153 A1 | 4/2008 | Ignagni | |
| 2008/0097513 A1 | 4/2008 | Kaji | |
| 2008/0208240 A1 | 8/2008 | Paz | |
| 2008/0208241 A1 | 8/2008 | Weiner | |

FOREIGN PATENT DOCUMENTS

| | | |
|---|---|---|
| WO | 0355420 | 7/2003 |
| WO | 2004093753 | 11/2004 |
| WO | WO2005018417 | 3/2005 |
| WO | WO2006/118744 | 11/2006 |
| WO | WO2006/128979 | 12/2006 |
| WO | WO2006/133927 | 12/2006 |
| WO | WO2007/027812 | 3/2007 |
| WO | WO2007/142503 | 12/2007 |

* cited by examiner

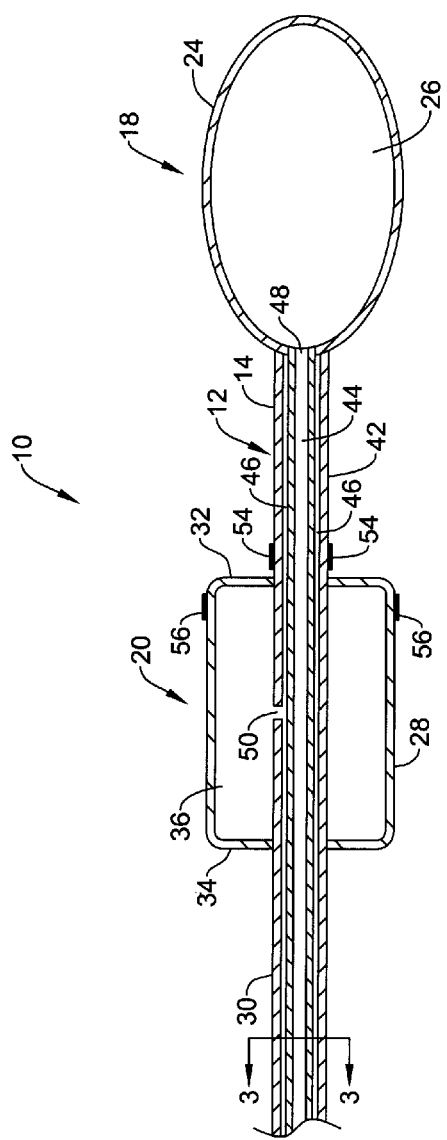

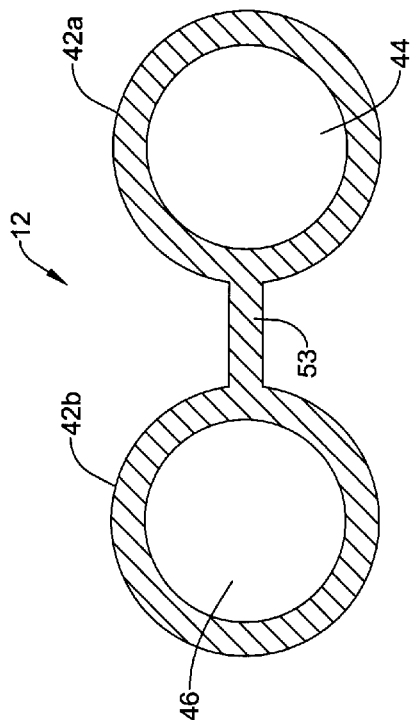
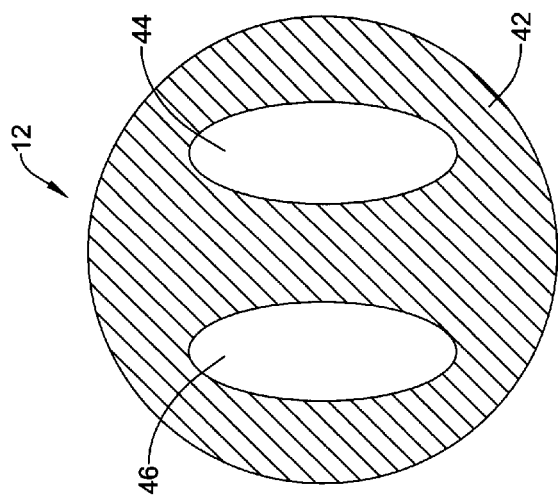
Figure 6
Figure 5

PERCUTANEOUS INTRAGASTRIC BALLOON DEVICE AND METHOD

RELATED APPLICATION

This Application claims the benefit of U.S. Provisional Application No. 60/676,641, filed on May 2, 2005.

FIELD

The present invention relates generally to the field of implantable medical devices for use in the treatment of obesity. More specifically, the present invention pertains to percutaneous intragastric balloon devices and methods for reducing food intake in patients suffering from obesity.

BACKGROUND

Obesity is a major medical problem affecting millions of individuals worldwide. In the United States alone, one in every two individuals is overweight, and one in every three individuals is obese. In addition to the psychosocial stigmas associated with such condition, overweight individuals often have a higher risk of acquiring significant debilitative illnesses such as insulin resistance, diabetes, hypertension, hyperlipidemia, degenerative arthritis, and atherosclerotic heart disease. Certain types of cancer, gallstones, varicose veins, thromboembolism, and hernias are also more prevalent among overweight individuals. Patients suffering from the condition often have a higher risk of surgical complications, which can lead to future life-threatening events such as myocardial infarction or ischemia. Weight loss often results in a significant reduction in these and other risks, and has been shown to significantly improve the mental health of obese individuals by improving their self-esteem and sense of well-being. The importance of proper weight management for obese individuals thus cannot be overemphasized.

The treatment of obesity typically includes lifestyle modifications such as regular exercise as well as certain dietary restrictions. The efficacy of such treatments is often low, however, since many obese patients are either unwilling or unable to comply with such behavioral changes. In some treatments where vigorous exercise is recommended to achieve an increase in energy output, the patient may be at greater risk of causing further damage to the body due to myocardial events associated with increased heart rates and physical exertion.

One treatment method for obesity involves the use of herbs, supplements, and/or pharmaceuticals to either increase metabolism or suppress appetite. While some stimulative and appetite suppressive drugs have had a limited success in the treatment of obesity, they rarely result in a satisfactory and sustained weight reduction. In some cases, the use of such drugs may be contraindicated, particularly for those individuals that may suffer from side-effects or who are at risk of becoming addicted. In addition, drug tolerance may also develop as a result of long-term use, reducing the effectiveness of such drugs to combat obesity for sustained periods of use. Other factors such as drug interactions and high cost may also limit the use of such drugs.

For morbidly obese patients (i.e. for those with a BMI over 40 or a BMI over 35 with co-morbidities), more invasive bariatric surgical procedures have been used to treat obesity. Some of these procedures may involve reducing the volume of the gastric cavity, for example, by creating a small pouch gastric bypass, or reducing the expansion capacity of the gastric cavity by placing a constrictive band around the stomach. Although bariatric surgery is frequently effective in combating obesity, such procedures are often more expensive and have higher complication and mortality rates.

As a less invasive technique to bariatric surgery, intragastric balloons were introduced in the early 1980's for treating obesity by partially filling the patient's stomach to produce a feeling of satiety or fullness. Such devices typically included a balloon that can be endoscopically inserted into the gastric cavity via the esophageal tube, and then inflated to partially fill to patient's stomach. Once inflated within the stomach, the distension caused by the balloon as well as by the presence of food stimulates various neuroreceptors located in the upper fundus of the stomach, causing the patient to experience an earlier feeling of fullness during meals. Continued use of the balloon typically results in a decrease in the daily caloric intake of the patient and subsequently a sustained weight loss.

Despite their effectiveness as a less invasive technique for treating obesity, many conventional intragastric balloons were initially limited to use in short-term programs of limited weight reduction, often prior to a more definitive bariatric surgery. A significant problem associated with these intragastric balloons was initially related to the manufacturing materials used, which were affected by the gastric acid within the stomach such that frequent replacement of the balloon was required. Other difficulties such as balloon rupture and/or migration also led to obstruction of the pylorus and the bowels in some patients, thus requiring additional surgery. In certain applications, the difficultly associated with placement of the balloon through the esophageal tube and the subsequent maintenance of the balloon once placed within the stomach also limit the effective use of such devices.

To overcome many of these drawbacks, more recent trends have focused on the use of percutaneous intragastric balloons for performing percutaneous gastronomy procedures on obese patients. In contrast to free-floating balloons, percutaneously inserted intragastric balloons are often secured in position via a support member such as a catheter or rod, typically at a location exterior of the patient's skin. While such devices overcome the problem of balloon migration and secondary bowel obstruction common in free-floating balloons, such devices are often difficult to place and maintain within the body. In addition, such devices often do not adequately address problems occurring at the placement site such as instability of the support catheter, gastric wall bleeding, and gastric content leak with the potential for peritonitis. Intolerance issues such as vomiting and abdominal pain as well as the embarrassment associated with the use of an extracorporeal device may further limit the use of such devices. Accordingly, there remains a need for effective solutions for the treatment of obesity.

SUMMARY

The present invention pertains to percutaneous intragastric balloon devices and methods for reducing food intake in patients suffering from obesity. An intragastric balloon device in accordance with an illustrative embodiment of the present invention may include a support catheter, a main balloon member for use in reducing the functional gastric capacity of the patient's stomach, a support balloon member for anchoring the intragastric balloon device to the gastric wall of the patient, and an inflation mechanism for use in selectively inflating the main and support balloon members.

The main balloon member can include an inflatable balloon configured to expand to a shape corresponding generally to the interior contour of the patient's stomach, providing the patient with a feeling of satiety or fullness. The support balloon member, in turn, can include one or more support balloons configured to expand and seal an opening formed through the gastric wall of the patient, thus preventing any leaking of gastric contents from the stomach as well as any bleeding from the gastric wall. The inflation mechanism can include a number of inflation chambers that can be used to selectively inflate or deflate each of the main and support balloon members once positioned within the body. In some embodiments, the inflation mechanism can include a means to attach the mechanism within the subcutaneous tissue of the patient so that the entire intragastric balloon device is located underneath the patient's skin.

An illustrative method of performing percutaneous gastronomy within the stomach of a patient using the intragastric balloon device may include the steps of percutaneously inserting the device into the patient's body and advancing at least a portion of the device through the abdominal wall and gastric wall and into the stomach, inflating the support balloon member within the patient's body to anchor the intragastric balloon device to the gastric wall, inflating the main balloon member within the stomach to at least partially fill the stomach, and then percutaneously inserting the inflation mechanism into the patient's body and then subcutaneously attaching the inflation mechanism to the patient's rectus abdominus muscle. The initial incision location for the insertion of the intragastric balloon device can be determined via an upper endoscopy using an endoscope inserted through the esophageal tube and into the stomach. In certain methods, an optional insertion device can be provided to facilitate insertion of the intragastric balloon device into the patient's body, if desired.

BRIEF DESCRIPTION OF THE DRAWINGS

FIG. 2 is a longitudinal cross-sectional view showing the intragastric balloon device along line 2-2 in FIG. 1;

FIG. 5 is a transverse cross-sectional view showing a catheter shaft configuration in accordance with another embodiment having a side-by-side lumen configuration;

FIG. 6 is a transverse cross-sectional view showing a catheter shaft configuration in accordance with another embodiment utilizing two side-by-side catheter shafts;

DETAILED DESCRIPTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized. While the illustrative insertion and operational steps described herein are shown with respect to human patients, it should be understood that the present invention could also be employed in veterinary applications for the treatment of other mammals.

Figure 1:
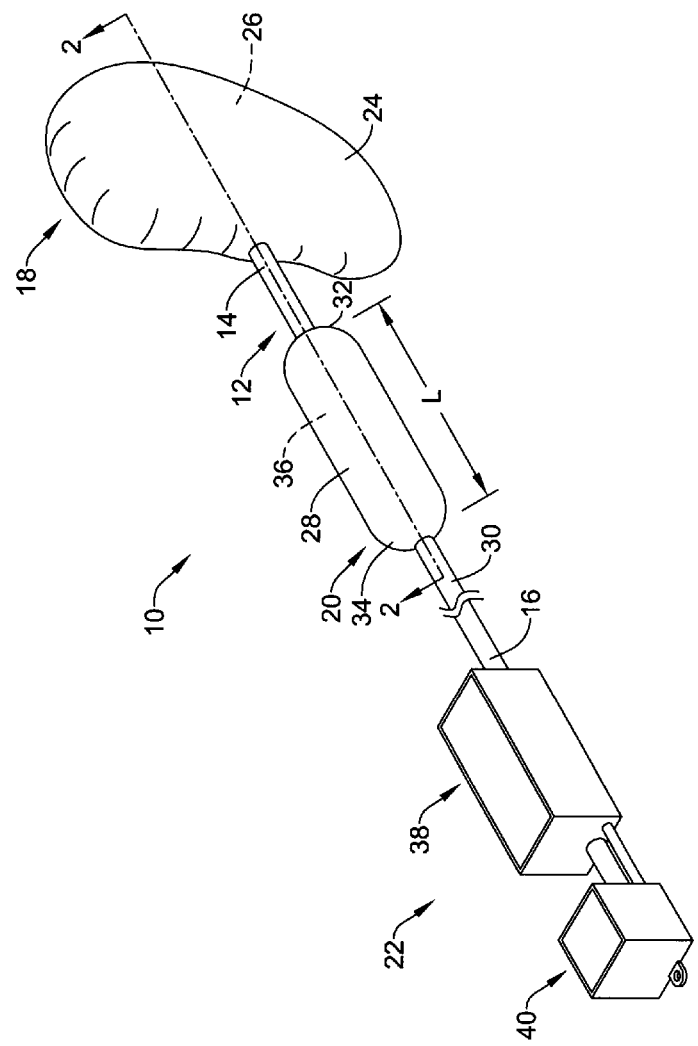
FIG. 1 is a perspective view of an intragastric balloon device in accordance with an exemplary embodiment of the present invention.

FIG. 1 is a perspective view of an intragastric balloon device 10 in accordance with an exemplary embodiment of the present invention. As shown in FIG. 1, intragastric balloon device 10 may include a support catheter 12 having a proximal section 14 and a distal section 16, a main balloon member 18 that can be expanded within the patient's stomach, and a support balloon member 20 that can be used to anchor the intragastric balloon device 10 to the gastric wall of the patient. The intragastric balloon device 10 may further include an inflation mechanism 22, which as is described in greater detail below, can be used to selectively inflate and deflate the main and support balloon members 18,20.

The main balloon member 18 can be configured to expand from an initial, low-profile position to an expanded position at least partially filling the patient's gastric cavity, thus reducing the capacity of the stomach and providing the patient with a feeling of satiety. As shown in an expanded position in FIG. 1, the main balloon member 18 can include an elongated-shaped balloon 24 having an interior cavity 26 adapted to contain a fluid such as air, saline, and/or water. The shape of the balloon 24 can be configured so as to generally match the interior contour of the stomach, which helps to reduce interference with the passage of gastric contents through the stomach and into the gastric outlet. In the illustrative embodiment of FIG. 1, for example, the balloon 24 may have a kidney-shaped configuration that deforms generally to the interior contour of the patient's gastric wall. In an alternative embodiment, and as shown, for example, in FIG. 7, the balloon 24 may have a substantially spherical shape. Other balloon shapes are possible, however. To reduce the risk of gastric ulceration along the gastric mucosa of the stomach, the balloon 24 can have a substantially smooth surface with rounded edges. If desired, the outer surface of the balloon 24 can also include a layer or coating of polytetrafluoroethylene (PTFE) or other lubricious material, which further facilitates the passage of gastric contents through the stomach.

The size of the balloon 24 can be adjusted depending on the volume of the patient's stomach, patient tolerance, patient response, the desired amount of satiety, as well as other factors. In certain embodiments, for example, the balloon 24 can be inflated from between about 20 ml to about 1000 ml, which is typically sufficient for inducing satiety in most adult individuals. It should be understood, however, that the size of the balloon 24 can be adjusted for use in other applications where a greater or lesser amount of satiety is desired, or where the intragastric balloon device 10 is to be used for other types of patients such as children or animals.

The balloon 24 can be formed from a suitably elastic, durable, and biocompatible material adapted to resist gastric acid and enzymes within the stomach. An example of such material may include medical grade silicon rubber, which is both resilient and durable to permit the intragastric balloon device 10 to remain in the body for extended periods of time, if needed. It should be understood, however, that other suitable materials exhibiting elasticity and durability could also be used, if desired. In certain embodiments, the balloon 24 can be formed from a distensible material, allowing the balloon 24 to expand and change shape depending on the pressure contained within the interior cavity 26. Alternatively, and in other embodiments, the balloon 24 can be formed from a non-distensible material that maintains the general shape of the balloon 24 as it is inflated within the patient's stomach.

The support balloon member 20 can be configured to expand from an initial, low-profile position to an expanded position for sealing a small opening formed through the gastric wall, thus anchoring the intragastric balloon device 10 within the patient's body while also preventing any leaking of gastric contents from the stomach and any bleeding from the gastric wall. As with the main balloon member 18, the support balloon member 20 can be formed from a suitable elastic, durable, and biocompatible material adapted to withstand gastric acid, enzymes, and other such materials within the body.

In the illustrative embodiment of FIG. 1, the support balloon member 20 includes a single support balloon 28 having a substantially cylindrical shape disposed about the side 30 of the support catheter 12. The support balloon 28 may have a proximal end 32, a distal end 34, and an interior cavity 36 adapted to contain a fluid such as saline or water. When positioned and expanded within the patient's body, the proximal end 32 of the support balloon 28 can be configured to normally lie at a position within the stomach a short distance beyond the interior of the gastric wall. The distal end 34 of the support balloon 28, in turn, can be configured to normally lie at a position within the tissue surrounding the exterior of the gastric wall. Typically, the length L of the support balloon 28 will exceed the thickness of the gastric wall by a short distance to ensure that the balloon 28 entirely fills the opening formed through the gastric wall.

The inflation mechanism 22 can be connected to the distal section 16 of the support catheter 12, and may define a number of inflation chambers 38,40 that can be used to provide fluid to the main and support balloon members 18,20. A first inflation chamber 38 of the inflation mechanism 22, for example, contains a source of fluid in fluid communication with the interior cavity 26 of the main balloon member 18 for inflating the main balloon member 18 within the patient's stomach. A second inflation chamber 40 of the inflation mechanism 22, in turn, contains a second source of fluid in fluid communication with the interior cavity 36 of the support balloon member 20 for selectively inflating and anchoring the support balloon member 20 to the gastric wall. As is discussed in greater detail below, the inflation mechanism 22 can be secured to the patient's body at a location within the subcutaneous tissue anterior the gastric wall, allowing the entire intragastric balloon device 10 to be situated within the body during use.

FIG. 2 is a longitudinal cross-sectional view showing the illustrative intragastric balloon device 10 along line 2-2 in FIG. 1. As can be further seen in FIG. 2, the support catheter 12 may include a thin tubular catheter shaft 42 defining a first inflation lumen 44 in fluid communication with the main balloon member 18 and the first chamber 38 of the inflation mechanism 22, and a second inflation lumen 46 in fluid communication with the support balloon member 20 and the second chamber 40 of the inflation mechanism 22. The first inflation lumen 44 may extend along substantially the length of the tubular shaft 42, having a first end (not shown) that terminates within the first chamber 38 of the inflation mechanism 22, and a second end 48 thereof terminating within the interior cavity 26 of the main balloon member 18. The second inflation lumen 46, in turn, may extend along substantially the length of the tubular shaft 42, having a first end (not shown) that terminates within the second chamber 40 of the inflation mechanism 22, and a second end thereof terminating within a side opening 50 of the catheter shaft 42 in communication with the interior 36 lumen of the support balloon member 20.

The catheter shaft 42 can be formed from a material or combination of materials adapted to maintain a desired level of axial strength and kink resistance while also permitting sufficient bending or flexion to permit the physician to easily maneuver the device 10 through the patient's body. Examples of suitable materials that can be used in forming the catheter shaft 42 may include, but are not limited to, metals such as stainless steel (e.g. 304V, 316L, etc.), polymers such as polyether block amide (PEBA), polyethylene terapthalate (PET), polytetrafluoroethylene (PTFE), or metal-polymer composites such as stainless steel reinforced hypotube.

Figure 4:
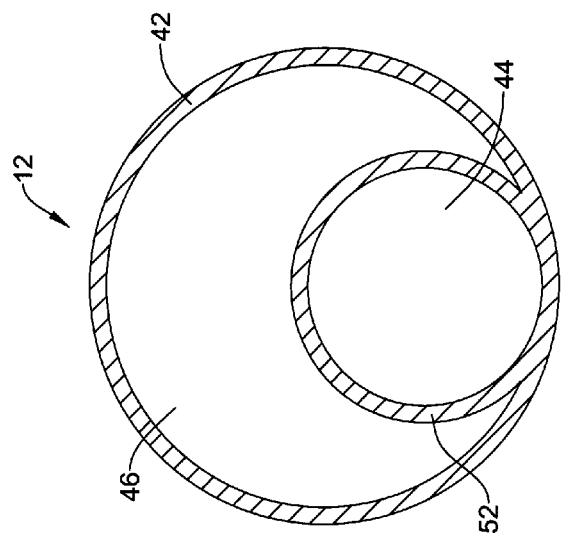
FIG. 4 is transverse cross-sectional view showing a catheter shaft configuration in accordance with another embodiment having an offset lumen configuration.
Figure 3:
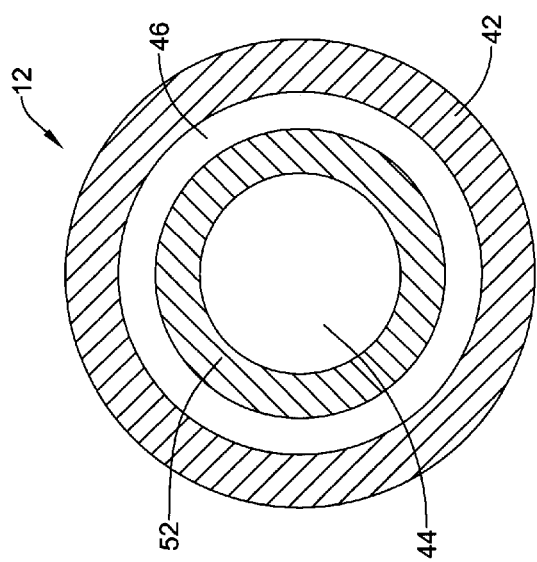
FIG. 3 is a transverse cross-sectional view showing the intragastric balloon device along line 3-3 in FIG. 2.

FIG. 3 is a transverse cross-sectional view showing the catheter shaft 42 along line 3-3 in FIG. 2. As can be seen in FIG. 3, the catheter shaft 42 may have a substantially circular transverse cross-section with the first inflation lumen 44 defining an interior, circular lumen and the second inflation lumen 46 defining an outer, annular-shaped inflation lumen. The first inflation lumen 44 can be separated from the second inflation lumen 46 via an interior tubular wall 52, which extends lengthwise in a direction along the general longitudinal axis of the catheter shaft 42. While the illustrative embodiment of FIG. 3 shows a circular catheter shaft 42 having a second inflation lumen 46 coaxially disposed about the first inflation lumen 44, it should be understood that other catheter shaft and lumen configurations are possible. In one alternative embodiment having an offset lumen configuration shown in FIG. 4, for example, the first inflation lumen 44 can be offset relative to the center of the catheter shaft 42 such that the second inflation lumen 46 has a crescent-like shape. In another alternative embodiment having a side-by-side configuration shown in FIG. 5, the first and second inflation lumens 44,46 may extend laterally in a side-by-side manner through the interior of the catheter shaft 42.

While a single catheter shaft 42 may contain each of the inflation lumens 44,46, it should be understood that separate catheter shafts each carrying a respective fluid lumen may be employed. In one such embodiment depicted in FIG. 6, for example, the support catheter 12 may include two separate catheter shafts 42a,42b coupled together via a bridge 53, with each shaft 42a,42b defining a respective inflation lumen 44,46 for inflating the main balloon member 18 and support balloon member 20.

As can be further seen by reference back to FIG. 2, the intragastric balloon device 10 may further include a number of markers 54,56 that can be used to endoscopically visualize the position of the catheter shaft 42 and support balloon member 20 within the body. A first marker 54 located on the catheter shaft 42 adjacent and proximal to the proximal end 32 of the support balloon member 20, for example, can be utilized to confirm proper placement of the proximal end 32 near the inner gastric wall of the patient's stomach. A second marker 56 located on the support balloon member 20 distally of the first marker 54 and at the juncture of the member 20 with the inner gastric wall can be utilized to confirm proper positioning and expansion of the support balloon member 20 within the gastric wall opening. The first and second markers 54,56 can be spaced apart from each other (as measured along the length of the catheter shaft 42) by a distance of about 1 cm to 4 cm, and more specifically, about 1.5 cm to 2 cm.

The first and second markers 54,56 can be formed from any number of suitable materials that can be visualized using an endoscope. In some embodiments, the markers 54,56 can also include a radiopaque material that can be radioscopically visualized within the patient's body using a fluoroscope or other suitable instrument. Examples of suitable radiopaque materials can include, but are not limited to, gold, iridium, platinum, silver, tantalum, tungsten, bismuth sub carbonate $((BiO)_2CO_3)$, and barium sulfate $(BaSO_4)$. If desired, other markers can be used to visualize other portions of the intragastric balloon device 10 such as the main balloon member 18 and/or the inflation mechanism 22.

Figure 7:
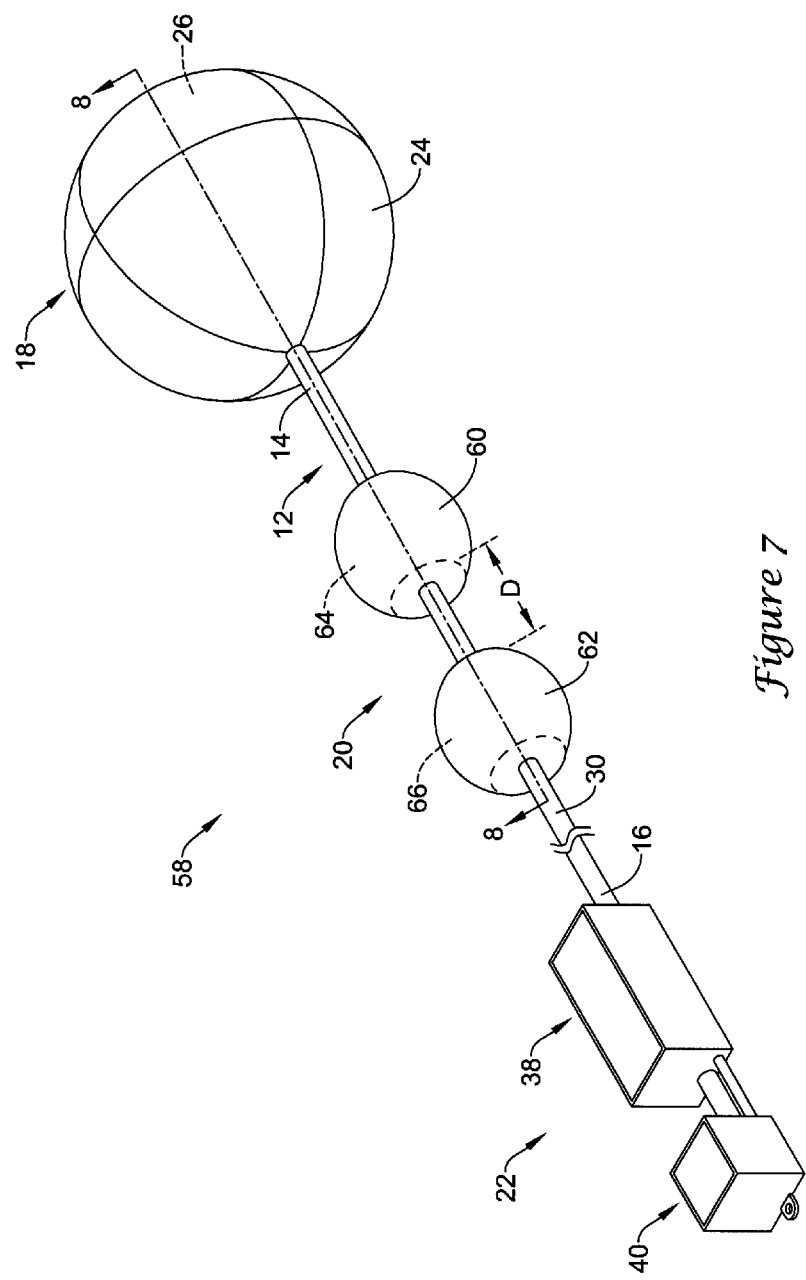
FIG. 7 is a perspective view of an intragastric balloon device in accordance with another exemplary embodiment of the present invention employing dual support balloons.

Referring now to FIG. 7, an intragastric balloon device 58 in accordance with another exemplary embodiment of the present invention employing dual support balloons will now be described. Intragastric balloon device 58 is similar in many respects to the intragastric balloon device 10 of FIG. 1, with like elements labeled in like fashion in the drawings. In the illustrative embodiment of FIG. 7, however, the support balloon member 20 used to anchor the intragastric balloon device 58 within the body includes two support balloons 60,62 each of which can be configured to expand from an initial, low profile position to an expanded position for sealing the interior and exterior portions of the gastric wall, respectively. A proximal support balloon 60, for example, can be configured to frictionally engage and seal the interior lining of the gastric wall, thereby preventing distal movement of the intragastric balloon device 58 through the gastric wall opening. Conversely, a distal support balloon 62 spaced apart a distance D of about 1 mm to 7 mm, and more specifically about 1.5 mm to 5 mm from the proximal support balloon 60 can be configured to frictionally engage and seal the exterior lining of the gastric wall, thereby preventing proximal movement of the intragastric balloon device 58 through the gastric wall opening. In some embodiments, the support balloons 60,62 can be configured to approximate from each other as they inflate, causing the proximal support balloon 60 to inflate in a direction towards the distal support balloon 62, and the distal support balloon 62 to inflate in a direction towards the proximal support balloon 60. In use, the proximal and distal support balloons 60,62 function by securing the intragastric balloon device 58 in place while preventing any leaking of gastric contents from the stomach and/or any bleeding from the gastric wall.

As shown in an inflated position in FIG. 7, each of the support balloons 60,62 can define a respective interior cavity 64,66, which when inflated with fluid from the second inflation chamber 40, causes the balloons 60,62 to expand and assume a substantially spherical shape that is slightly larger than the size of the gastric wall opening. The support balloons 60,62 can each be configured to expand to the same size and shape within the body, as shown, for example, in FIG. 7, or alternatively can be configured to assume different sizes and/or shapes therein. In certain embodiments, for example, the size or shape of the support balloons 60,62 can be varied slightly based on the specific anatomy of the patient.

Figure 8:
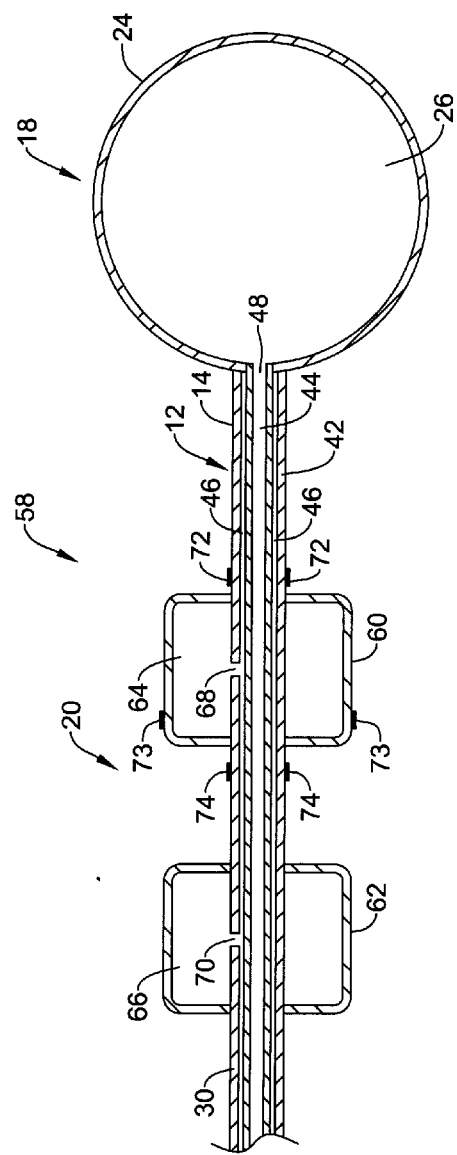
FIG. 8 is a longitudinal cross-sectional view showing the intragastric balloon device along line 8-8 in FIG. 7.

FIG. 8 is a longitudinal cross-sectional view showing the intragastric balloon device 58 along line 8-8 in FIG. 7. As can be further seen in FIG. 8, the interior cavity 64,66 of each support balloon 60,62 is in fluid communication with the second inflation lumen 46 via a number of respective openings 68,70 disposed through the side 30 of the catheter shaft 42. In this configuration, pressurized fluid delivered through the second inflation lumen 46 from the second inflation chamber 40 causes each of the support balloons 60,62 to simultaneously inflate about the support catheter 12.

A number of markers disposed on the catheter shaft 42 and the support balloon member 20 can be utilized to endoscopically visualize the intragastric balloon device 58 within the patient's body. The markers may include, for example, a first marker 72 located on the catheter shaft 42 adjacent and proximal to the first (i.e. proximal) support balloon 60, and a second marker 73 located on the first support balloon 60 distally from the first marker 72. In some embodiments, a third marker 74 located on the catheter shaft 42 distally of the second marker 73 and having a color different from the second marker 73 can be further provided. In use, and as discussed herein, the markers 72,73,74 can be utilized to confirm proper positioning of the intragastric balloon device 58 within the patient's body. If desired, other markers can be used to visualize other portions of the intragastric balloon device 58 such as the main balloon member 18 and/or the inflation mechanism 22.

Figure 9:
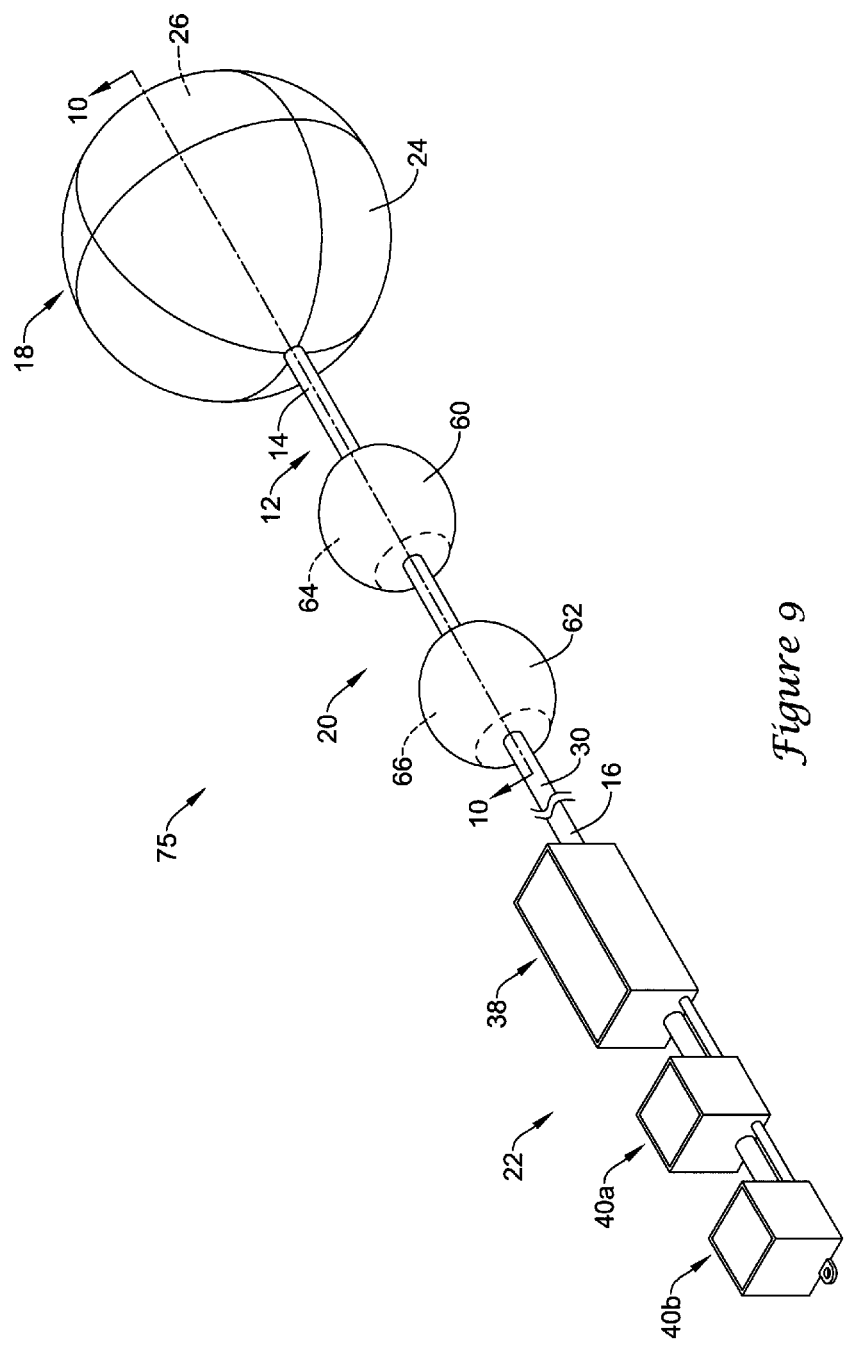
FIG. 9 is a perspective view of an intragastric balloon device in accordance with another embodiment of the present invention employing separately inflatable support balloons.

FIG. 9 is a perspective view of an intragastric balloon device 75 in accordance with another embodiment of the present invention employing separately inflatable support balloons. Intragastric balloon device 75 is similar to the intragastric balloon device 58 described above with respect to FIGS. 7-8, with like elements labeled in like fashion in the drawings. In the illustrative embodiment of FIG. 9, however, each of the support balloons 60,62 are separately inflatable within the body, which during insertion, allows the physician to initially inflate the first support balloon 60 against the inner wall of the stomach prior to immobilizing the support catheter 12 in place by inflating the second support balloon 62.

The inflation mechanism 22 for the illustrative intragastric balloon device 75 may define a number of inflation chambers 38,40a,40b that can be used to provide fluid to the main and support balloon members 18,20. The first inflation chamber 38 may contain a source of fluid in fluid communication with the interior cavity 26 of the main balloon member, as discussed herein. A second inflation chamber 40a of the inflation mechanism 22, in turn, may contain a second source of fluid in fluid communication with the interior cavity 64 of the first support balloon 60 for selectively inflating and anchoring the first support balloon 60 to the interior wall of the stomach. A third inflation chamber 40b, in turn, may contain a third source of fluid in fluid communication with the interior cavity 66 of the second support balloon 62 for selectively inflating and anchoring the second support balloon 62 to the exterior wall of the stomach.

Figure 10:
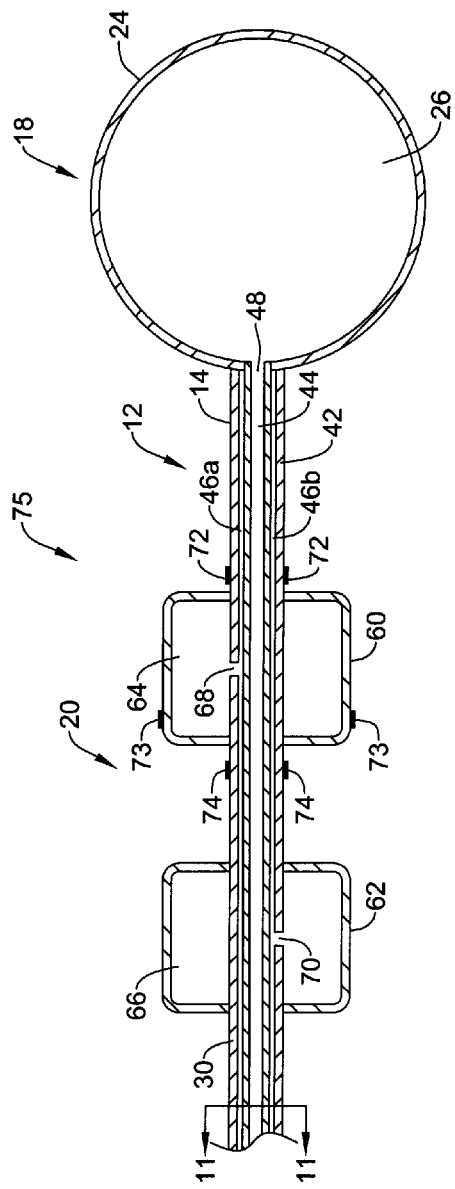
FIG. 10 is a longitudinal cross-sectional view showing the intragastric balloon device along line 10-10 in FIG. 9.

FIG. 10 is a longitudinal cross-sectional view showing the illustrative intragastric balloon device 75 along line 10-10 in FIG. 9. As shown in FIG. 10, the catheter shaft 42 of the support catheter 12 may define a first inflation lumen 44 in fluid communication with the main balloon member 18 and the first chamber 38 of the inflation mechanism 22, a second inflation lumen 46a in fluid communication with the first support balloon member 60 and the second chamber 40a of the inflation mechanism 22, and a third inflation lumen 46b in fluid communication with the second support balloon member 62 and the third chamber 40b of the inflation mechanism 22.

Figure 11:
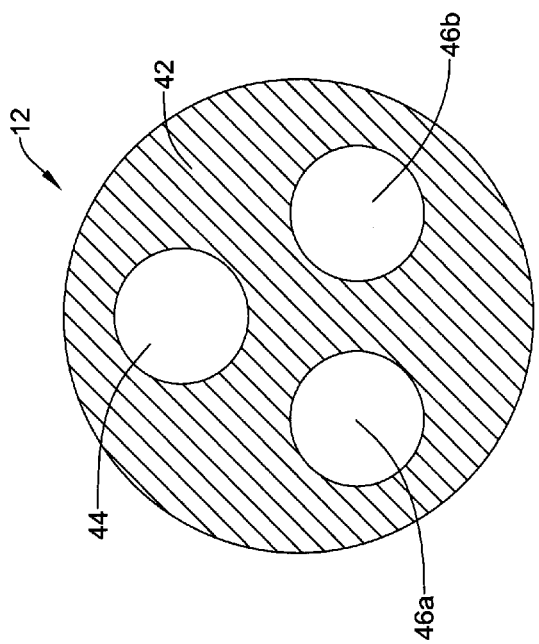
FIG. 11 is a transverse cross-sectional view showing the intragastric balloon device along line 11-11 in FIG. 10.

The first inflation lumen 44 may extend along substantially the length of the tubular shaft 42, having a first end (not shown) that terminates within the first chamber 38 of the inflation mechanism 22, and a second end 48 thereof terminating within the interior cavity 26 of the main balloon member 18. The second inflation lumen 46a may extend along substantially the length of the tubular shaft 42, having a first end (not shown) that terminates within the second chamber 40a of the inflation mechanism 22, and a second end thereof terminating within a side opening 68 of the catheter shaft 42 adjacent the first support balloon 60. The third inflation lumen 46b, in turn, may extend along substantially the length of the tubular shaft 42, having a first end (not shown) that terminates within the third chamber 40b of the inflation mechanism 22, and a second end thereof terminating within a side opening 70 of the catheter shaft 42 adjacent the second support balloon 62. A transverse cross-sectional view showing an illustrative arrangement of the lumens 44,46a,46b within the catheter shaft 42 may be further seen, for example, with respect to FIG. 11, which shows the lumens 46a,46b used to inflate the support balloons 60,62 having a side-by-side configuration. It should be understood, however, that other lumen configurations are possible.

Figure 12:
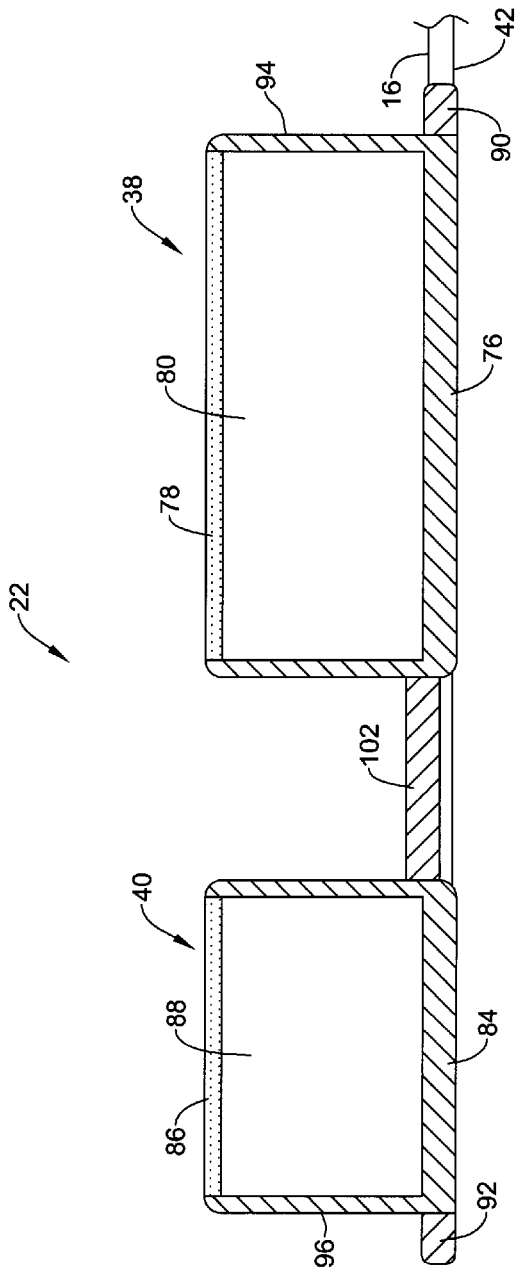
FIG. 12 is a side cross-sectional view showing the inflation mechanism of FIG. 1 in greater detail.

Referring now to FIG. 12, the inflation mechanism 22 for the illustrative intragastric balloon devices 10,58 will now be described in greater detail. As shown in cross-section in FIG. 12, the first inflation chamber 38 can include a support base 76 and a self-sealing elastomeric lid 78, which together define an interior cavity 80 adapted to contain a pressurized source of saline, water, air, or other suitable biocompatible fluid and/or gas for inflating the main balloon member 18. The support base 76 can be formed from a biocompatible material or combination of materials having a sufficient strength to support the pressurized fluid within the interior cavity 80. Examples of such materials may include metals such as surgical stainless-steel or platinum, and/or polymeric materials such as polyethylene, polyurethane, or polysulfone. If desired, the edges of the first inflation chamber 38 can be chamfered to reduce trauma to the body.

The self-sealing elastomeric lid 78 can be formed from an elastic, biocompatible material such as silicon rubber, which can be configured to self-seal when punctured with a syringe needle, puncturing trocar, or other piercing instrument. The elastomeric lid 78 can be configured to automatically seal to prevent the passage of fluid out of the interior cavity 80 when the piercing instrument is inserted through the lid 78 and, subsequently, when the instrument is removed from the first inflation chamber 38.

The second inflation chamber 40 can be configured similar to the first inflation chamber 38, including a support base 84 and a self-sealing elastomeric lid 86 which together define an interior cavity 88 adapted to contain a pressurized source of fluid for inflating the support balloon member 20. In certain embodiments, the second inflation chamber 40 can be made slightly smaller than the first inflation chamber 38, allowing the physician to visually identify each of the inflation chambers 38,40 during the insertion process and subsequently during use. In addition, and in some embodiments, the second inflation chamber 40 can contain a fluid having a different color from that of the first inflation chamber 38, allowing the physician to further distinguish between the two inflation chambers 38,40 as fluid is injected into or withdrawn from the interior cavities 80,88. In certain embodiments, for example, the fluid contained in the first inflation chamber 38 can be substantially clear or opaque whereas the fluid contained within the second inflation chamber 40 can have a visually discernable color such as red or green. It should be understood, however, that other color combinations could be used to permit the physician to distinguish between the two inflation chambers 38,40, if desired.

Figure 13:
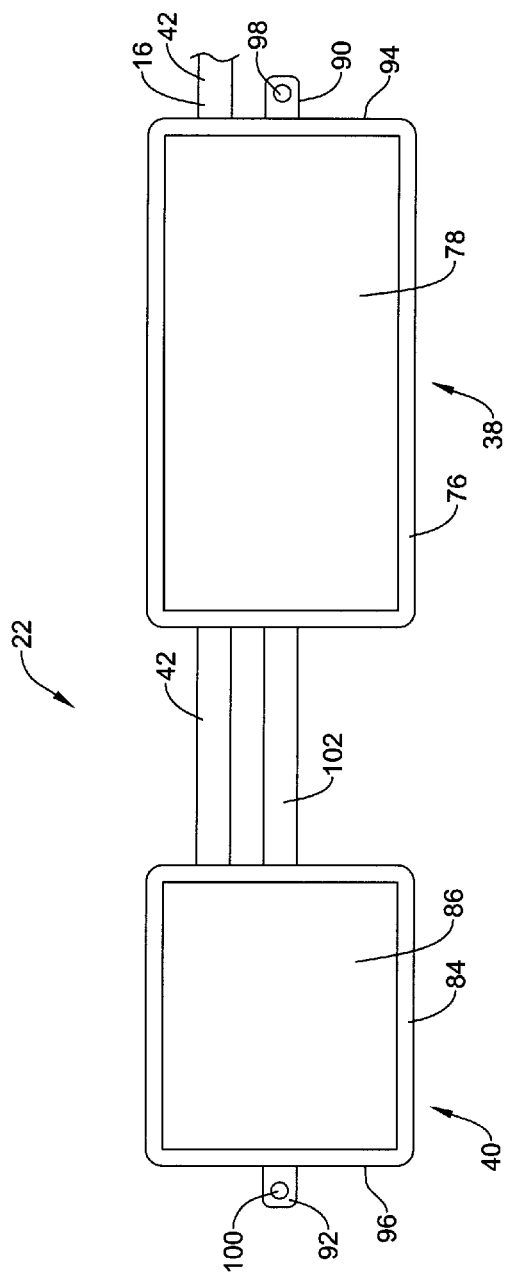
FIG. 13 is a top perspective view of the illustrative inflation mechanism of FIG. 12.

FIG. 13 is a top perspective view of the illustrative inflation mechanism 22 of FIG. 12. As can be further understood with respect to FIG. 13, stabilizing rings 90,92 coupled, respectively, to the peripheral ends 94,96 of each support base 76,84 can be provided to attach the inflation mechanism 22 subcutaneously to adjacent muscle mass within the patient's body using a number of sutures or stables. In certain applications, for example, a number of sutures or staples can be used to attach each of the stabilizing rings 90,92 to the patient's rectus abdominus muscle, thus securing the inflation mechanism 22 at a position below the surface of the patient's skin within the subcutaneous tissue surrounding the patient's abdomen. Attachment of the sutures or stables can be accomplished, for example, using a number of holes or openings 98,100 disposed through the stabilizing rings 90,92.

A connection bridge 102 may be used to interconnect the support bases 76,84, and can be used as a third attachment point for attaching the inflation mechanism 22 to the patient's body, if desired. In certain embodiments, the connection bridge 102 may be formed from a short (e.g. 2 cm to 4 cm) band, ligament, or wire made from a biocompatible material such as silicon rubber or stainless-steel. In use, the connection bridge 102 can be configured to permit slight movement of the first inflation chamber 38 relative to the second inflation chamber 40 to accommodate any movement of the adjacent muscle mass.

The inflation mechanism 22 for use with the illustrative intragastric balloon device 75 of FIG. 9 can be configured similar to that described above, with each inflation chamber 38,40a,40b including a support base and self-sealing elastomeric lid defining an interior cavity adapted to contain a fluid or gas. The fluid or gas contained within each of the chambers 38,40a,40b may have a different color from each other, allowing the physician to distinguish between each of the chambers 38,40a,40b during inflation. In certain embodiments, for example, the fluid contained in the first inflation chamber 38 can be substantially clear or opaque whereas the fluid in the second and third chambers 40a,40b may each have a visually discernable color such as blue and red, respectively.

In certain applications, insertion of the intragastric balloon device 10,58,75 can be accomplished using an optional insertion device that can be used by physician to facilitate percutaneous insertion of the device 10,58,75 through the patient's skin, abdominal wall, gastric wall and into the gastric cavity of the stomach. As discussed herein, the insertion device may generally include a large pore needle (e.g. a G14 or G16) having a length of about 3 to 5 inches, a guidewire having a length of about 25 cm to 35 cm adapted to slidably fit through an interior lumen of the large pore needle, a number of dilators for piercing the abdominal and gastric walls, and a guide member that can be used to facilitate insertion of the intragastric balloon device 10,58,75 into the patient's body.

Figure 14:
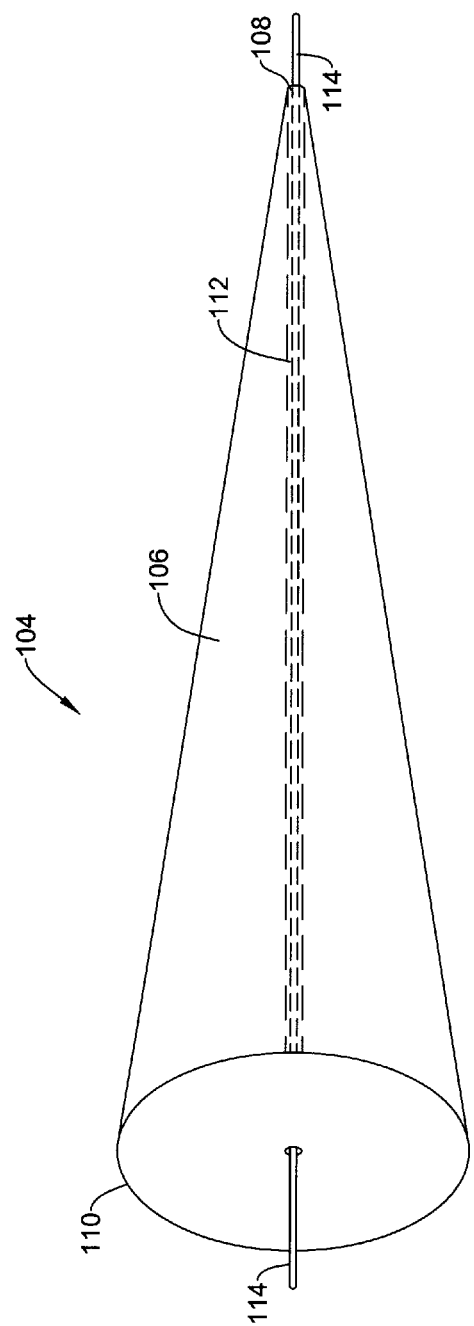
FIG. 14 is a schematic view of an illustrative introducer dilator for use with an intragastric balloon device.

FIG. 14 is a schematic view of an illustrative introducer dilator 104 for use with the intragastric balloon devices 10,58, 75. As shown in FIG. 14, the introducer dilator 104 can have a tapered tubular body 106 including a first end 108, a second end 110, and an interior lumen 112 adapted to slidably receive a guidewire 114. The introducer dilator 104 can have a substantially conical shape with the first end 108 having a relatively low transverse profile for insertion through the abdominal and gastric walls, and the second end 110 having a relatively large transverse profile for use in manipulating the dilator 104 at a position outside of the patient's body. The tubular body 106 can be formed from a relatively rigid polymeric and/or metallic material, allowing the physician to advance the first end 108 into the patient's body by applying a pushing force on the second end 110. In use, the introducer dilator 104 can be used to facilitate insertion of the intragastric balloon device 10,58,75 into the body by dilating the opening within abdominal and gastric walls.

Figure 15:
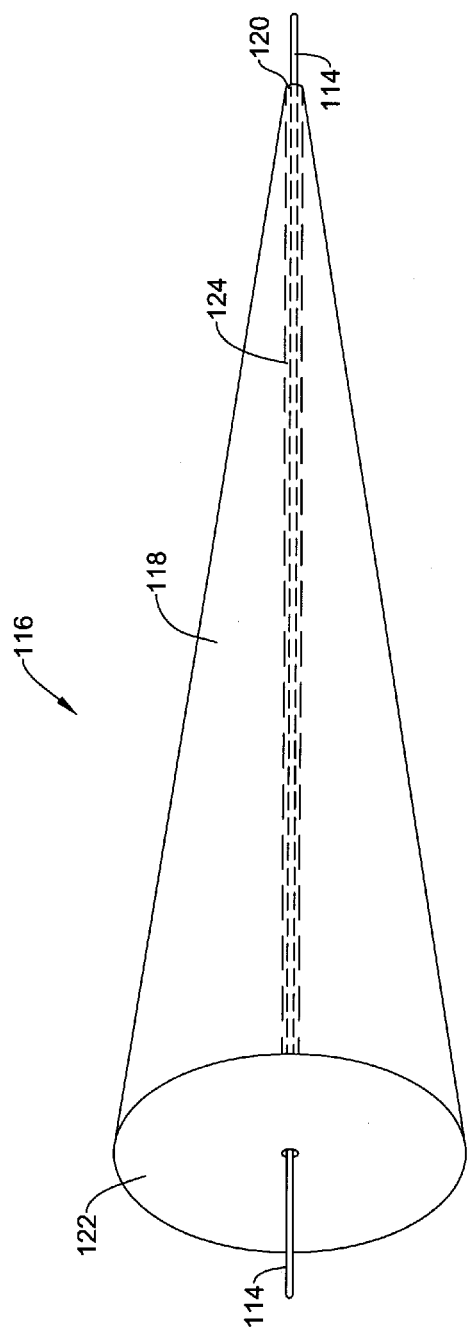
FIG. 15 is a schematic view of an illustrative second dilator for use with an intragastric balloon device.

FIG. 15 is a schematic view of a second dilator 116 for use with the intragastric balloon device 10,58,75. As shown in FIG. 15, the second dilator 116 can have a tapered tubular body 118 including a first end 120, a second end 122, and an interior lumen 124 adapted to slidably receive the guidewire 114. The second dilator 116 may have a substantially conical shape similar to that of the introducer dilator 104, with the first end 120 having a relatively low transverse profile for insertion through the abdominal wall and gastric wall, and the second end 122 having a relatively large transverse profile for use in manipulating the dilator 116 at a position outside of the patient's body. In some embodiments, the second dilator 116 may be sized slightly different than the introducer dilator 104 to facilitate distension of the gastric wall opening when inserted therethrough.

Figure 16:
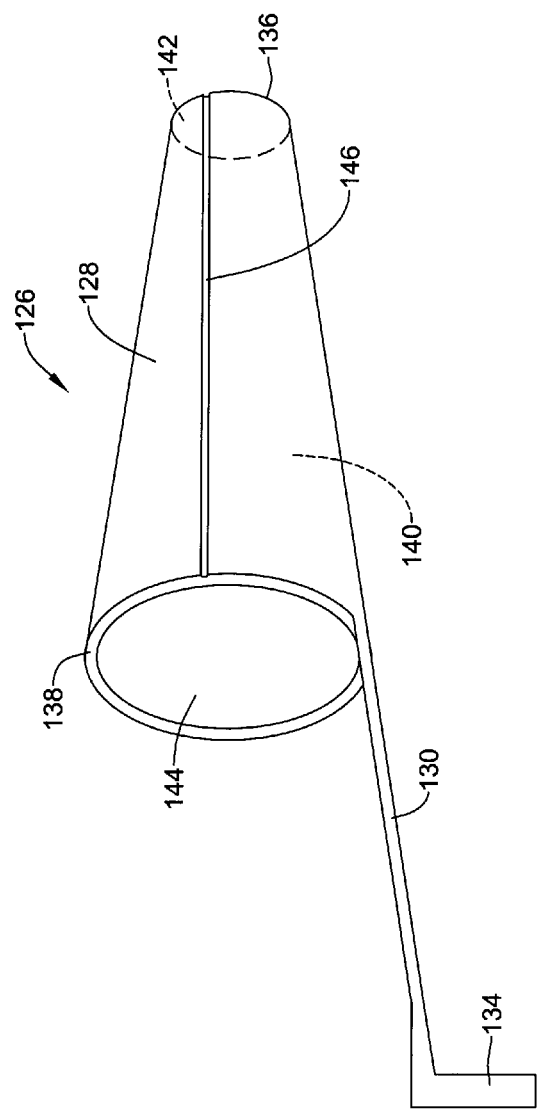
FIG. 16 is a schematic view of an illustrative guide member for use with an intragastric balloon device.

FIG. 16 is a schematic view of an illustrative guide member 126 for use with the illustrative intragastric balloon device 10,58,75. As shown in FIG. 16, the guide member 126 can include a tubular body 128 coupled to a support arm 130 and handle 134 that can be manipulated by the physician's hand from a position outside of the patient's body. While a single support arm 130 and handle 134 are shown in the illustrative embodiment of FIG. 16, it should be understood that the guide member 126 may include two support arms and handles to permit the physician to manipulate the guide member 126 with both hands, if desired.

The tubular body 128 of the guide member 126 can be formed from a durable and rigid polymeric material, and can have a frustroconical shape including a first end 136, a second end 138, and an interior lumen 140 adapted to slidably receive the main tubular body 118 of the second dilator 116 therein. The interior lumen 140 may extend through the entire length of the tubular body 128, defining a first, relatively small opening 142 at the first end 136 of the body 128, and a second, relatively large opening 144 at the second end 138 thereof. The interior lumen 140, including both the first and second openings 142,144, can be dimensioned to permit the passage of the intragastric balloon device 10,58,75 in a deflated position through the tubular body 128 during insertion of the device 10,58,75 into the patient's body. As can be further seen coupled to the second dilator 116 in FIG. 17, for example, the interior lumen 140 of the guide member 126 can be dimensioned to slidably receive a portion of the second dilator 116, allowing the physician to insert the second dilator 116 into the guide member 126, advance both the second dilator 116 and guide member 126 into the patient's body, and then subsequently remove the second dilator 116 to permit insertion the intragastric balloon device 10,58,75 through the interior lumen 140 of the guide member 126.

Figure 17:
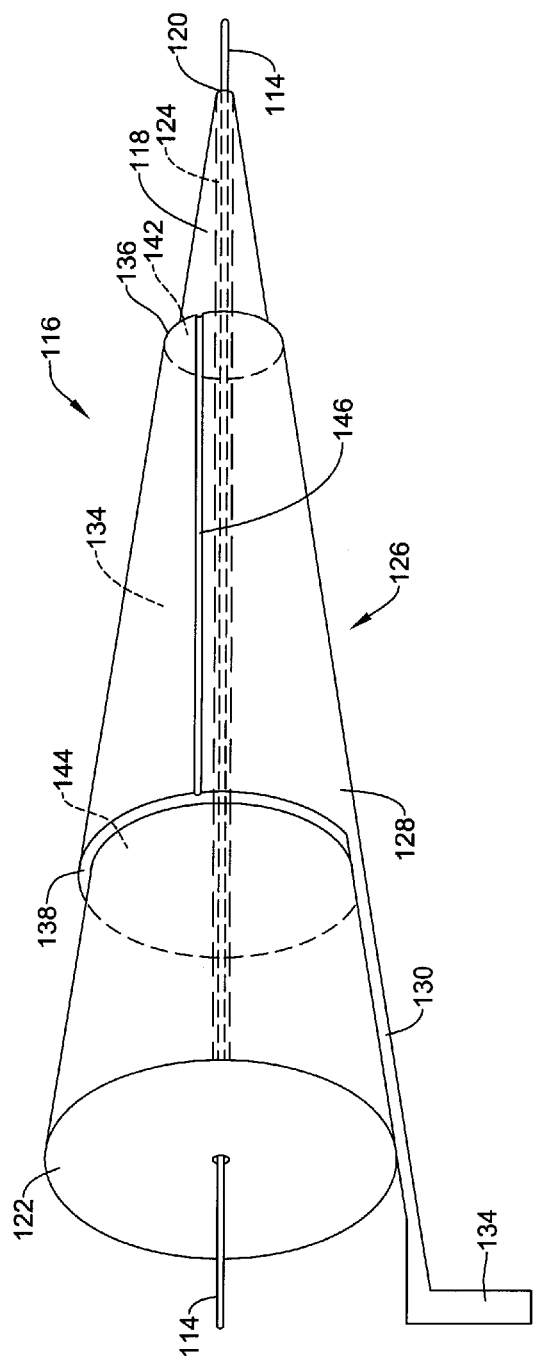
FIG. 17 is a schematic view showing the insertion of the second dilator of FIG. 15 into the guide member of FIG. 16.
Figure 18:
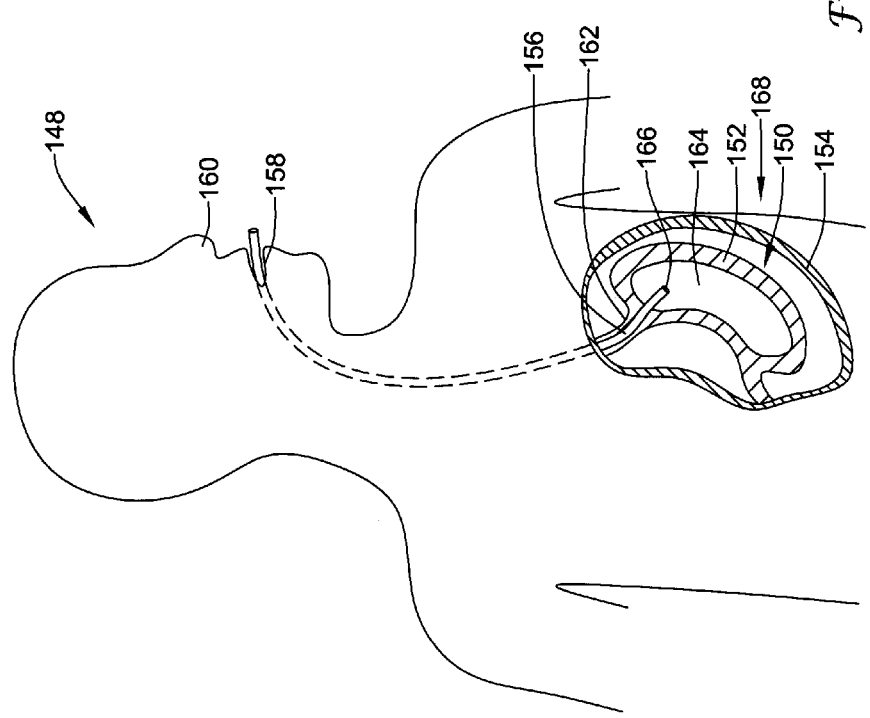
FIG. 18 is a fragmentary cross-sectional view showing an endoscope inserted into a patient's stomach.
Figure 19:
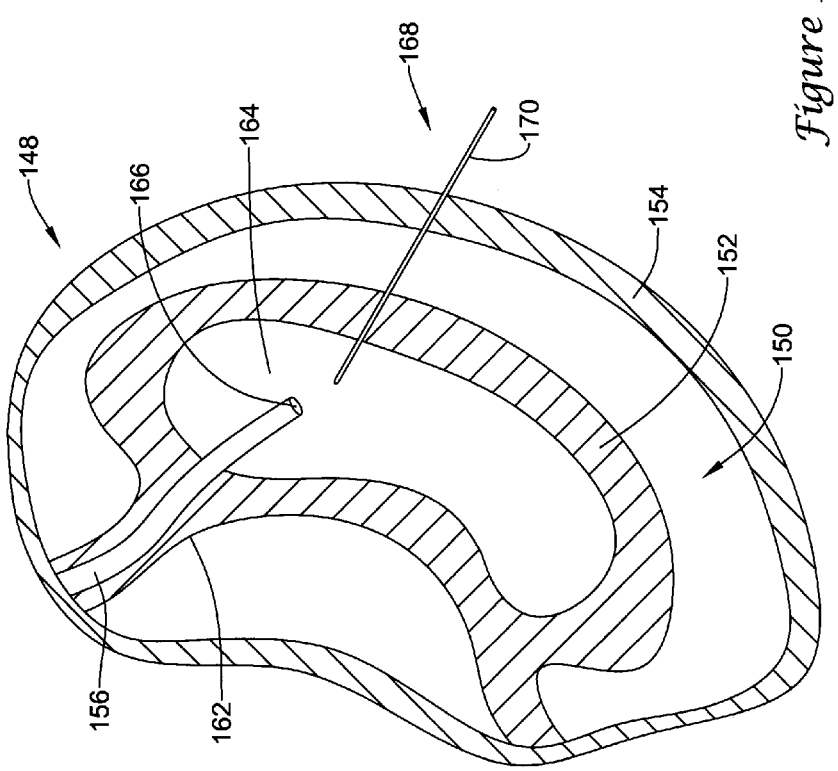
FIG. 19 is an enlarged fragmentary cross-sectional view showing the insertion of a large pore needle into the stomach of FIG. 18.
Figure 20:
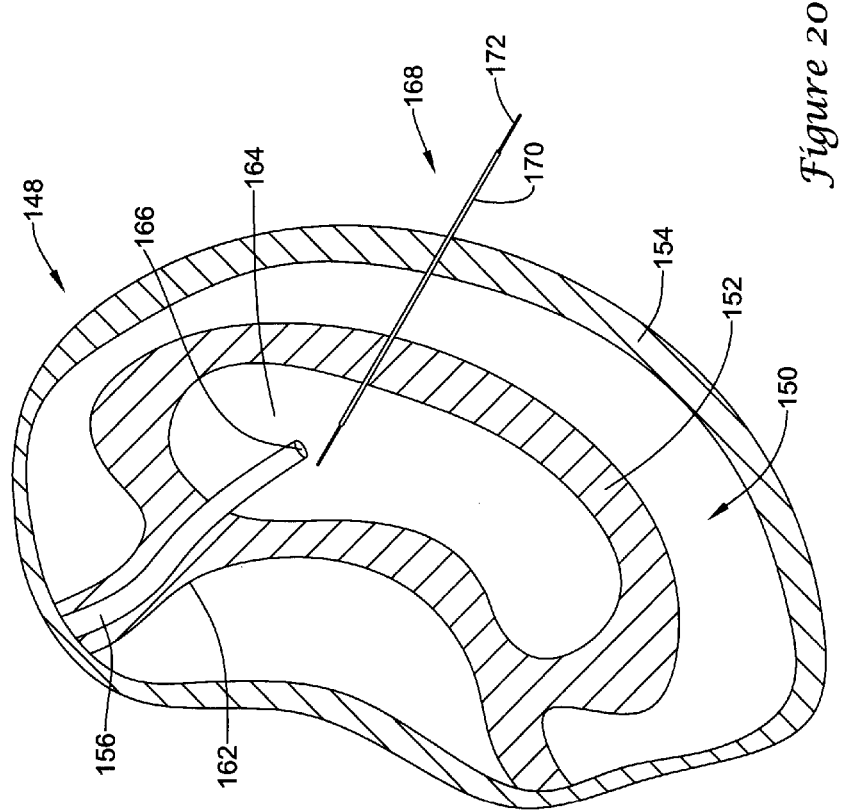
FIG. 20 is an enlarged fragmentary cross-sectional view showing the insertion of a guidewire into the stomach of FIG. 18.

To facilitate removal of the guide member 126 after insertion of the intragastric balloon device 10,58,75, and as further shown in FIGS. 16 and 17, a cutting line 146 can be provided along the length of the guide member body 128. The cutting line 146 may include, for example, a thinned or perforated portion of the body 128, allowing the physician to cut and peel-away the guide member 126 from the support catheter 12 after the intragastric balloon device 10,58,75 has been positioned within the patient's body.

Referring now to FIGS. 18-26, an illustrative method of performing a percutaneous gastronomy procedure on a patient 148 will now be described with respect to the intragastric balloon devices 10,58,75 described above. In preparation for the procedure, the patient is placed under conscious sedation, and as shown in a first view in FIG. 18, a central view flexible endoscope 156 can be inserted into either the patient's mouth 158 or nasal cavity 160 through the esophagus 162 and into the gastric cavity 164 of the stomach 150. Once inserted therein, the patient's stomach 150 is then inflated with air until the anterior gastric wall 152 pushes against the abdominal wall 154. The light emitted from the leading end 166 of the endoscope 156 is then directed towards the anterior gastric wall 152 and visualized through the abdominal wall 154. The incision site 168 in the epigastric area of the patient 148 can then be determined by the physician based in part on the light visualized through the abdominal wall 154.

Once the incision site 168 has been determined, and in further preparation for the procedure, the patient's skin can be cleaned with a topical microbicide such as Betadine®, and then draped. The skin is infiltrated with a local anesthetic such as lidocain with an epinephrine solution, and a large pore needle 170 (e.g. a G16 or G14) having a length of about 3 to 5 inches can then be inserted through the abdominal wall 154 and the gastric wall 152 under direct intragastric visualization using the endoscope 156, as further shown in a subsequent view in FIG. 19. A guidewire 172 having a length of about 25 cm to 35 cm can then be introduced through the large poor needle 170 and into the gastric cavity 164 of the stomach 150, also under direct visualization via the endoscope 156, as further shown in a subsequent view in FIG. 20.

Figure 21:
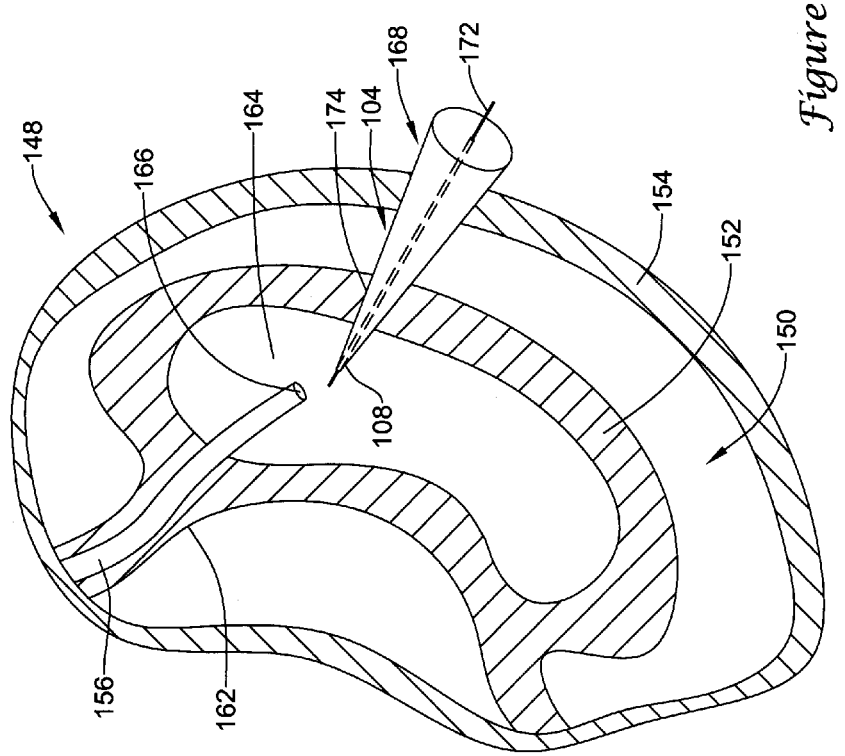
FIG. 21 is an enlarged fragmentary cross-sectional view showing the insertion of an introducer dilator into the stomach of FIG. 18.
Figure 22:
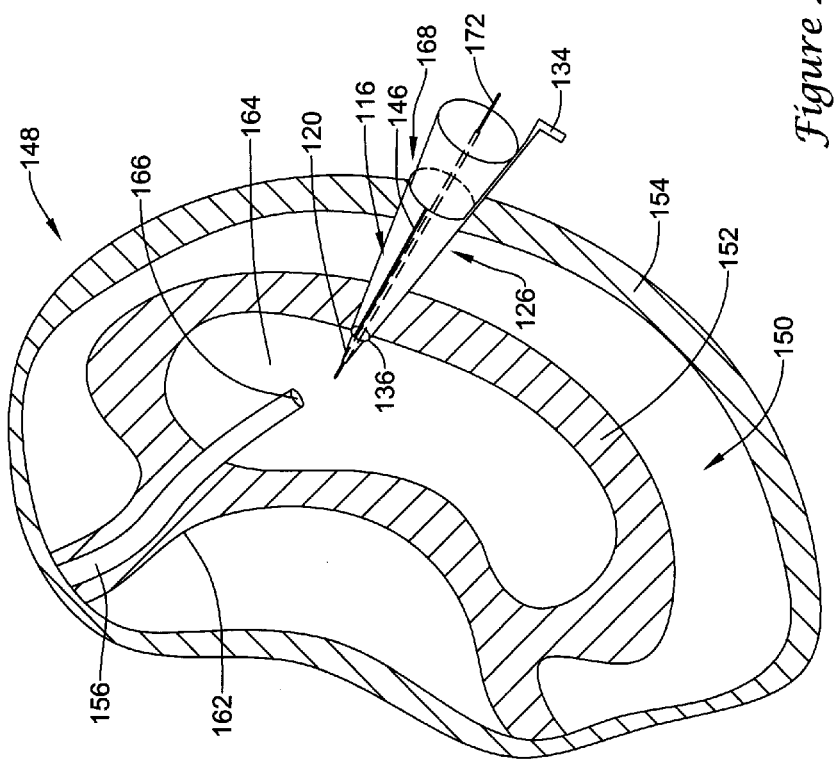
FIG. 22 is an enlarged fragmentary cross-sectional view showing the insertion of a second dilator and guide member into the stomach of FIG. 18.

With the guidewire 172 inserted through the abdominal wall 154 and gastric wall 152, the large poor needle 170 can then be removed and an incision made in the skin and subcutaneous tissue with a scalpel. In those embodiments in which an optional insertion device is to be used, the introducer dilator 104 can then be introduced over the guidewire 172 and advanced through the abdominal wall 154 and gastric wall 152 until the first end 108 of the dilator 104 is located within the gastric cavity 164 a short distance beyond the anterior gastric wall 152, as further shown in a subsequent view in FIG. 21. As can be seen in FIG. 21, the insertion of the introducer dilator 104 through the stomach 150 creates a small opening 174 within the gastric wall 152 that can be used to insert the leading end of the intragastric balloon device 10,58,75 into the gastric cavity 164 while the balloon members 18,20 are in their deflated position.

Once inserted through the gastric wall 152, the introducer dilator 104 can then be removed, and the second dilator 116 inserted into the guide member 126 in preparation for insertion of the second dilator 116 into the patient's body. Once the second dilator 116 is inserted into the guide member 126, the dilator 116 and guide member 126 can then be introduced over the guidewire 172 and inserted into the gastric cavity 164 through the abdominal wall 154 and gastric wall 152, as shown in a subsequent view in FIG. 22. Once the guide member 126 is positioned through abdominal wall 154 and gastric wall 152 with the first end 136 of the guide member 126 visualized inside the gastric cavity 164 via the endoscope 156, it is then immobilized in place using the handle 134. The second dilator 116 and guidewire 172 can then be withdrawn from the patient's body.

With the guide member 126 immobilized within the gastric wall 152, the intragastric balloon device 10,58,75 can then be inserted within the second lumen opening 144 of the guide member body 128 and advanced through the interior lumen 140 until the first marker 54,72 is visualized within the gastric cavity 164 and positioned approximately 3 cm from the gastric mucosa of the stomach 150. The intragastric balloon device 10,58,75 can then be immobilized in place, and the guide member 126 subsequently withdrawn from the patient's body. The guide member 126 is then cut along the cutting line 146 and removed from about the intragastric balloon device 10,58,75. The intragastric balloon device 10,58,75 can then be pulled a short distance until the second marker 56,73 is visualized at the gastric mucosa of the stomach 150, and the third marker 74 is no longer visible.

While insertion of the intragastric balloon devices 10,58,75 can be accomplished with the aid of the optional insertion device described herein, it should be understood that the above insertion steps can be performed without the use of such devices, if desired. In certain techniques, for example, insertion of the intragastric balloon device 10,58,75 can be accomplished by making an incision in the patient's skin that extends all the way through the abdominal and gastric walls 154,152 into the gastric cavity 164, subsequently followed by the insertion of the device 10,58,75 as described herein. Moreover, while the use of an introducer dilator 104 is depicted with respect to the illustrative step of FIG. 21, it should be understood that insertion of the second dilator 116 and guide member 126 can be accomplished without the use of the introducer dilator 104, if desired.

Once the intragastric balloon device 10,58,75 has been inserted and properly positioned within the patient's body, a predetermined amount of colored fluid can then be injected into the second inflation chamber 40 of the inflation mechanism 22, causing the support balloon member 20 to inflate within the patient's body. Injection of the colored fluid can be accomplished, for example, by injecting a syringe needle or other small-diameter cannula into the self-sealing elastic lid 86 of the second inflation chamber 40, and then injecting pressurized fluid into the interior cavity 88. Upon removal of the syringe needle, the elastic lid 86 can be configured to automatically reseal to prevent the escape of fluid within the interior cavity 88.

Figure 23:
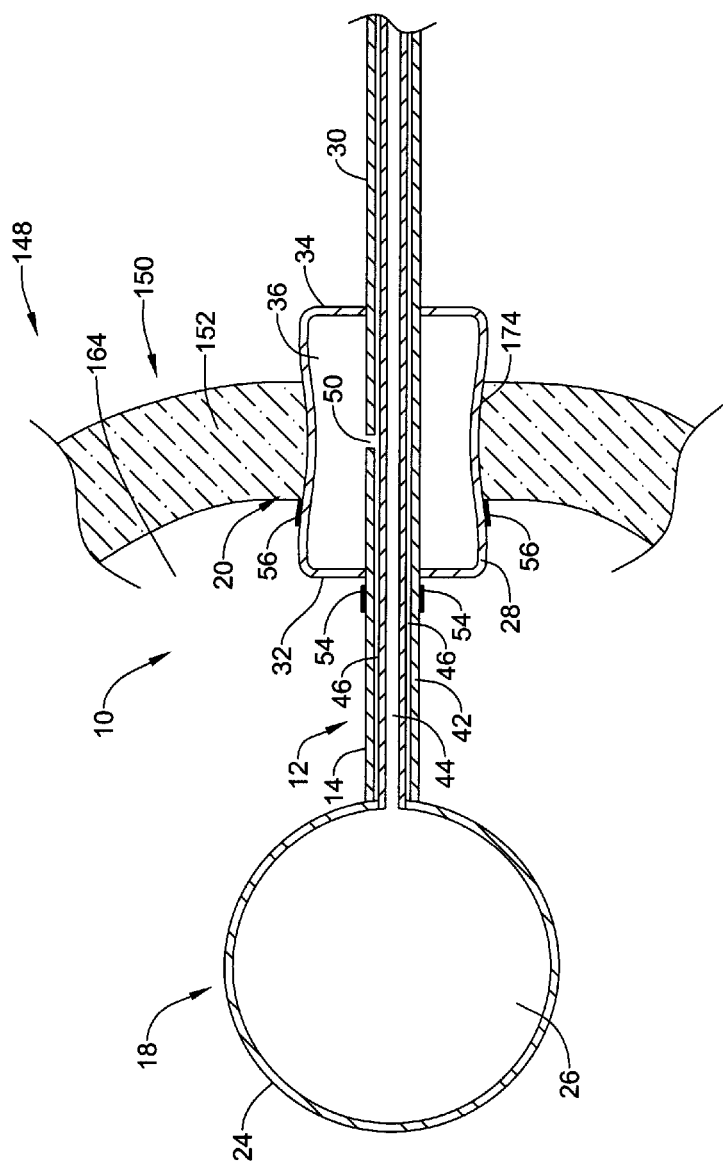
FIG. 23 is an enlarged fragmentary cross-sectional view showing the illustrative intragastric balloon device of FIG. 1 in an inflated position within the stomach of FIG. 18.
Figure 24:
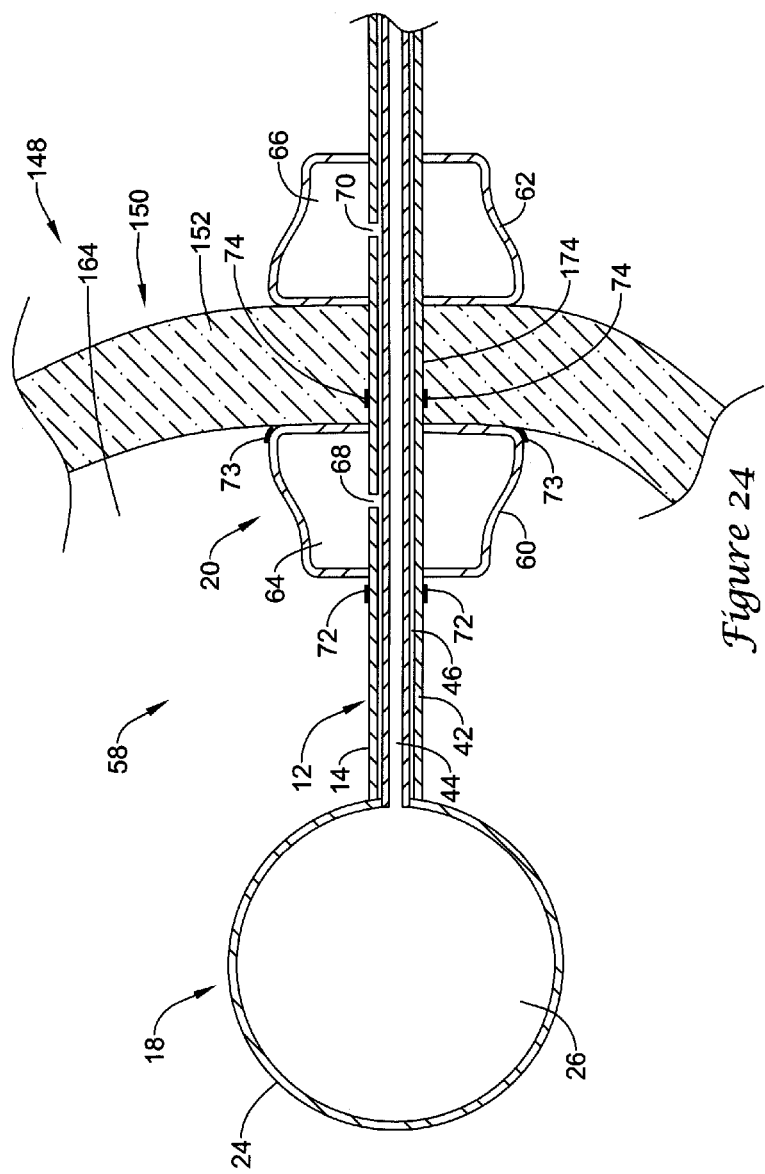
FIG. 24 is an enlarged fragmentary cross-sectional view showing the illustrative intragastric balloon device of FIG. 7 in an inflated position within the stomach of FIG. 18.

FIGS. 23-24 are enlarged fragmentary cross-sectional views showing the intragastric balloon devices 10,58 in an inflated position adjacent the gastric wall 152 of the patient 148. As can be seen with respect to intragastric balloon device 10 in FIG. 23, for example, radial expansion of the support balloon 28 causes the balloon 28 to compress against the gastric wall 152 and seal the gastric wall opening 174, thus controlling any bleeding from the gastric wall 152 and preventing any leakage of gastric contents from the gastric cavity 164. If desired, the proper positioning of the support balloon 28 can be visually and/or radiographically confirmed using the first and second markers 54,56.

In a similar manner, and as further shown in FIG. 24 with respect to the illustrative dual support balloon intragastric balloon device 58 described above, radial expansion of the two support balloons 60,62 causes the balloons 60,62 to compress on either side of the gastric wall 152 and seal the gastric wall opening 174, likewise controlling any bleeding from the gastric wall 152 and preventing any leakage of gastric contents contained within the gastric cavity 164. If desired, the proper positioning of the two support balloons 60,62 on either side of the gastric wall 152 can be visually and/or radiographically confirmed using the first and second markers 72,73. Before expansion of the support balloons 60,62, the balloon device 58 is slowly and carefully pulled until the optional third marker 74 becomes concealed within the gastric wall 152 and the second marker line 73 is visualized at the juncture of the device 58 with the gastric mucosa, providing the physician with visual feedback that the support balloons 60,62 are properly positioned, before and after their inflation.

In those embodiments where three inflation lumens are provided to permit the selective inflation of each of the support balloons 60,62, immobilization of the intragastric balloon device may be accomplished via an optional technique wherein each of the support balloons 60,62 are inflated at different times within the body. With respect to the illustrative intragastric balloon device 75 described above with respect to FIGS. 9-11, for example, the physician may advance the device 75 into the stomach 150 until the third marker 74 is visualized with the endoscope 156, inject a colored fluid (e.g. blue) into the second chamber 40a of the inflation mechanism 22 causing the first support balloon 60 to inflate and engage the interior wall of the stomach 150, pull the support catheter 12 a short distance distally until the first support balloon 60 pushes against the inside of the gastric wall 152, and then subsequently inject a different colored fluid (e.g. red) into the third chamber 40b of the inflation mechanism 22 causing the second support balloon 62 to inflate and engage the exterior wall of the stomach 150.

Once the support balloon member 20 has been expanded to secure the intragastric balloon device 10,58,75 to the gastric wall 152, the first inflation chamber 38 can then be injected with air or carbon dioxide followed by an amount of clear or opaque fluid, causing the main balloon member 18 to expand within the gastric cavity 164. In certain procedures, for example, approximately 15 ml to 20 ml of air is first injected into the first inflation chamber 38 followed by about 80 ml of clear saline or water, causing the main balloon member 18 to expand and partially fill the patient's stomach 150. It should be understood, however, that different quantities of fluids and/or air can be used to inflate the main balloon member 18 based on the volume of the patient's stomach, patient tolerance, patient response, the desired amount of satiety, as well as other factors.

Figure 25:
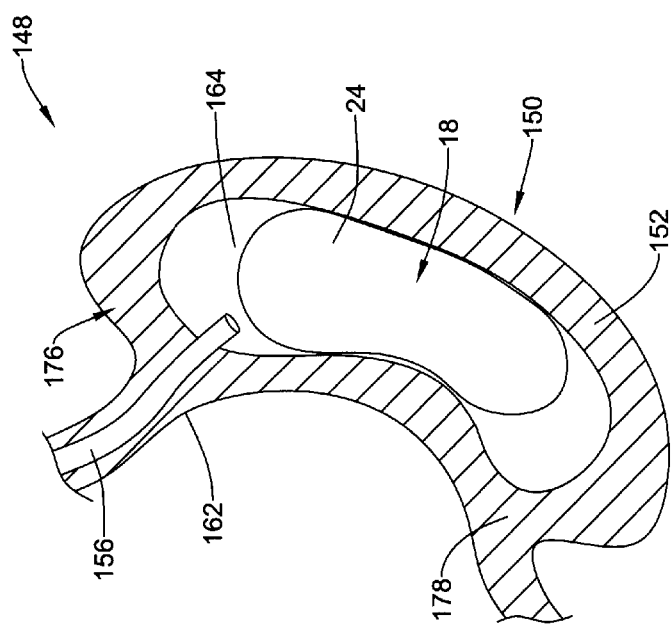
FIG. 25 is an enlarged fragmentary cross-sectional view showing the main balloon member inflated within the stomach of FIG. 18.

FIG. 25 is an enlarged fragmentary cross-sectional view showing the main balloon member 18 inflated within the patient's stomach 150. As shown in FIG. 25, when inflated within the patient's stomach 150, the main balloon member 18 can be configured to expand and assume an elongated shape within the gastric cavity 164 due in part to the air pocket formed by initially injecting air into main balloon member 18. For ease of illustration in FIG. 25, the catheter shaft 12 and support balloon member 20 have not been shown. It should be understood, however, that a portion of the catheter shaft 12 and support balloon member 20 will typically lie within the gastric cavity 164 along with the main balloon member 18, which acts to further reduce the size of the patient's stomach 150.

Typically, the main balloon member 18 will be positioned in the upper fundus 176 of the patient's stomach 150 where most of the neuroreceptors are located, thus providing the patient 148 with a greater feeling of satiety. The mixture of air and fluid will tend to keep the main balloon member 18 floating on top of the solid and liquid food in the upper anterior part of the stomach 150 and away from the pylorus 178, thus making gastric outlet obstruction less likely. In some cases, the existence of the air pocket within the main balloon member 18 may also reduce friction and pressure against the gastric wall 152, resulting in a lower risk of gastric ulceration.

Once the main balloon member 18 has been inflated to a desired size within the stomach 150, the physician may then remove the syringe needle from the first inflation chamber 38 and withdraw the endoscope 156. If desired, the physician may verify the proper positioning and inflation status of the main balloon member 18 using an abdominal X-ray, which can distinguish the air/fluid level within the balloon 24 from the gastric contents within the stomach 150.

Figure 26:
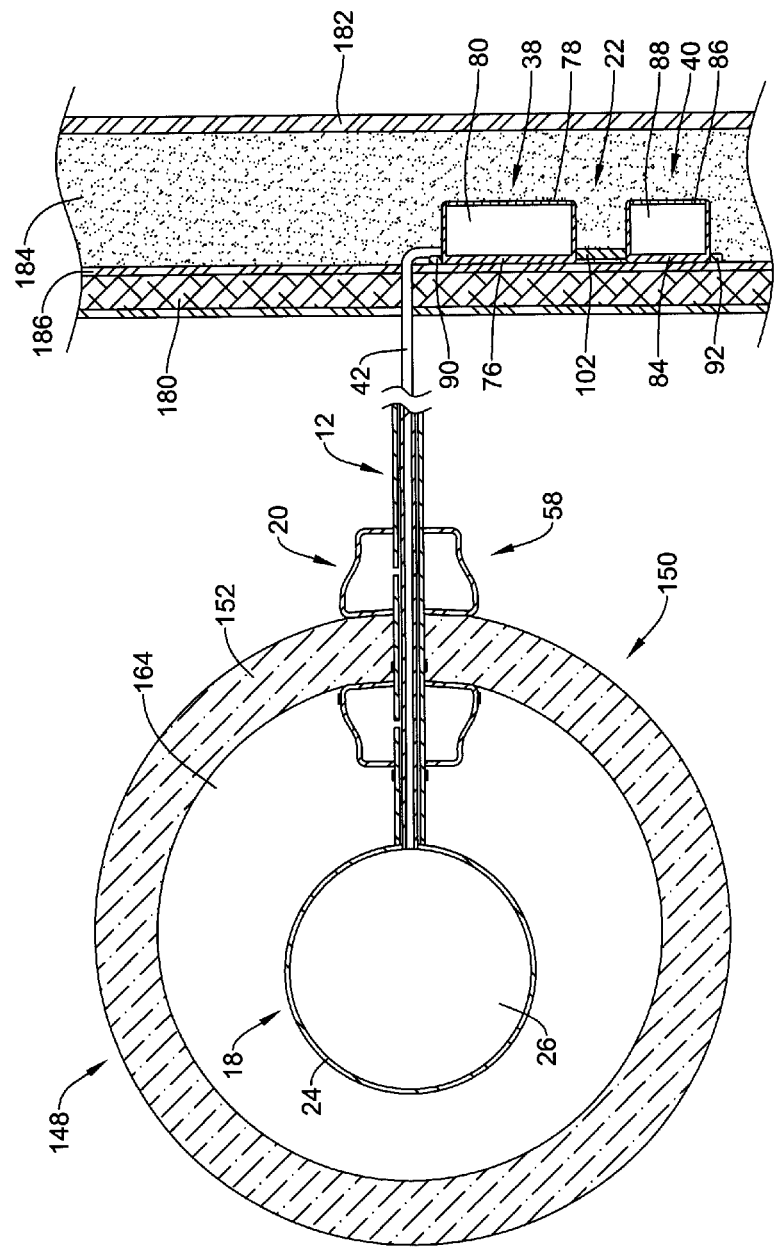
FIG. 26 is an enlarged fragmentary cross-sectional view showing an illustrative step of attaching the inflation mechanism to the patient.

FIG. 26 is an enlarged fragmentary view showing an illustrative step of attaching the inflation mechanism 22 of the illustrative intragastric balloon device 58 to the rectus abdominus muscle 180 of the patient 148. In preparation for insertion, an incision can be made through the patient's skin 182 and subcutaneous tissue 184. Once an incision has been made, the inflation mechanism 22 is then inserted into the subcutaneous tissue 184 and positioned such that the support bases 76,84 for each inflation chamber 38,40 are adjacent to the rectus muscle sheath 186.

In certain procedures, and as can be further seen in FIG. 26, the first inflation chamber 38 can be oriented above (i.e. cephalic) relative to the second inflation chamber 40 to facilitate later identification of each inflation chamber 38,40 once disposed underneath the patient's skin 182. Once positioned and oriented within the subcutaneous tissue 184, the physician can then secure the inflation mechanism 22 to the rectus muscle sheath 186 and rectus abdominus muscle 180 by suturing or stapling each of the stabilizing rings 90,92 and/or the connecting bridge 102 to the sheath 186 and muscle 180. Once secured, the incision is then closed, and an antibiotic ointment with dressing is applied. Because the entire intragastric balloon device 58 is located underneath the patient's skin 182, there is less discomfort, greater convenience, and a lower risk of secondary infection. In addition, other problems such as the social stigma associated with using extracorporeal intragastric balloon devices are also reduced or eliminated.

Subsequent to implantation within the body, the patient 148 can then be checked periodically to assess their tolerance to the intragastric balloon device 58 as well as to assure that acceptable pressures are maintained within each of the balloon members 18,20. If the physician determines that patient tolerance to the device 58 is acceptable but a more aggressive weight loss course is desired, the main balloon member 18 can be further inflated within the stomach 150 by inserting a syringe needle or other suitable cannula through the patient's skin 182 and into the first inflation chamber 38. An additional amount (e.g. 50 ml to 150 ml) of fluid can then be injected into the interior cavity 80, further shrinking the functional gastric volume resulting in an earlier feeling of satiety, less caloric intake and subsequently more weight loss. Conversely, if the physician determines that patient tolerance is poor, or if a less aggressive weight loss course is desired, fluid can be aspirated from the interior cavity 80 of the first inflation chamber 38, causing the main balloon member 18 to deflate and increase the functional gastric volume within the stomach 150.

If necessary, adjustment of the balloon members 18,20 can be accomplished using a syringe needle inserted into the appropriate one of the self-sealing lids 78,86 on the first and second inflation chambers 38,40. If, for example, the physician desires to adjust the size of the main balloon member 18 within the stomach 150, a syringe needle can be inserted through the patient's skin 182 and into the interior cavity 80 of the first inflation chamber 38. In preparation for insertion, a local anesthetic such as a lidocain patch can be placed on the patient's skin 178, which can then be cleaned with alcohol. Once the syringe needle is inserted into the first inflation chamber 38, confirmation of the needle position can be made by applying a negative pressure to the syringe needle, causing some of the clear fluid contained within the first inflation chamber 38 to be drawn into the syringe. After visually confirming the presence of the clear fluid within the syringe, the physician can then either inject or aspirate the desired amount of fluid into or out of the main balloon member 18, as desired. If desired, the pressure within the main balloon member 18 can be verified using a pressure gauge attached to the syringe needle. The syringe needle can then be withdrawn from the first inflation chamber 38 and removed from the patient's body.

Adjustment of the support balloon member 20 can be accomplished in a similar manner using a second syringe needle inserted through the patient's skin 182 and into the interior cavity 88 of the second inflation chamber 40. A similar preparation and confirmation process as used for the main balloon member 18 can be performed to anesthetize and clean the patient's skin and visually confirm the presence of colored fluid within the second inflation chamber 40. After visually confirming the presence of the colored fluid within the syringe, the physician can then either inject or aspirate a desired amount of fluid into or out of the support balloon member 20, as desired. If desired, the pressure within the support balloon member 20 can be verified using a pressure gauge attached to the syringe needle. The syringe needle can then be withdrawn from the second inflation chamber 40 and removed from the patient's body.

At the conclusion of the patient's weight loss program, or if further use of the intragastric balloon device 58 is undesired, the physician may then remove the intragastric balloon device 58 from the patient's body. In preparation for removal, the patient's skin can be cleaned using a topical microbicide such as Betadine®, and then draped. Local anesthesia can then be achieved by infiltrating the skin with a local anesthetic such as lidocain with an epinephrine solution. Once prepared, an incision can be made in the skin at the same location as the initial placement scar, or at some other location, if desired. The inflation mechanism 22 can then be detached from the patient's rectus abdominus muscle 180 by removal of the stabilizing stitches. The balloon members 18,20 can then both be completely deflated by inserting syringe needles into each of the inflation chambers 38,40 and drawing out any excess fluid contained therein.

With the balloon members 18,20 in a deflated position, the intragastric balloon device 58 can then be withdrawn from the patient's body. If the physician desires to replace the intragastric balloon device 58 with another such device, the above insertion steps can be repeated, either with or without the use of the optional insertion device described above. Alternatively, if the physician wishes to remove the intragastric balloon device 58, the physician may withdraw the device 58 and then seal the gastric wall 152, the rectus abdominus muscle 180, and the skin 182 by suturing, stapling or other suitable means. Replacement and/or removal of the intragastric balloon device 58 can be accomplished with or without the aid of an endoscope, as desired.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes can be made with respect to various elements described herein without exceeding the scope of the invention.

What is claimed is:

1. An intragastric balloon device comprising: a catheter having a proximal end, a distal end and a catheter shaft disposed therebetween, a main balloon fluid lumen, a first support balloon fluid lumen, and a second support balloon fluid lumen;
    an unconstrained main balloon member coupled to the catheter and in fluid communication with the main balloon fluid lumen, the main balloon member adapted to expand between a first position and a second position within a patient's stomach for reducing the functional gastric capacity of the stomach;
    an unconstrained proximal support balloon member coupled to and encircling an outer surface of the catheter shaft and in fluid communication with the first support balloon fluid lumen, the proximal support balloon member being expandable between a first deflated position and a second inflated position to provide a distal facing anchoring surface;
    an unconstrained distal support balloon member coupled to and encircling the outer surface of the catheter shaft and in fluid communication with the second support balloon fluid lumen, said distal support balloon member longitudinally spaced from the proximal support balloon member and expandable between a first deflated position and a second inflated position to provide a proximal facing anchoring surface, wherein the proximal facing anchoring surface, the distal facing anchoring surface, and the outer surface of the catheter shaft between the longitudinally spaced distal and proximal support balloon members define an annular channel structured to receive the patient's gastric wall therein for anchoring the balloon device to the patient's gastric wall, wherein said main balloon member, said proximal support member and said distal balloon support member are non-integrally formed from balloon material and distinct one from the other;
    at least one inflation chamber that defines a substantially fixed volume and is structured and arranged to be implanted subcutaneously, said at least one inflation chamber in direct fluid communication with said main balloon fluid lumen and said first and second support balloon fluid lumens, said at least one inflation chamber structured to selectively and independently inflate the main and support balloon members;
    an insertion device for use in percutaneously inserting and implanting the intragastric balloon device within the patient's body;
    a dilator including a tapered tubular body having a proximal end, a distal end, and an interior lumen adapted to slidably receive a guidewire; and
    a guide member operatively coupled to the dilator and including a tubular body and at least one support arm and handle, said tubular body defining an interior lumen adapted to slidably receive the intragastric balloon device, and wherein said intragastric balloon and said inflation chamber are configured to be implanted in a patient until a desired weight loss is achieved.

2. The intragastric balloon device of claim 1, wherein the tubular body of said guide member includes a cutting line.

* * * * *